United States Patent
Sasaki

(10) Patent No.: US 9,895,138 B2
(45) Date of Patent: Feb. 20, 2018

(54) ULTRASONIC DIAGNOSTIC APPARATUS

(75) Inventor: Takuya Sasaki, Nasu-gun (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1254 days.

(21) Appl. No.: 13/608,399

(22) Filed: Sep. 10, 2012

(65) Prior Publication Data

US 2013/0006111 A1    Jan. 3, 2013

Related U.S. Application Data

(63) Continuation of application No. PCT/JP2012/064584, filed on Jun. 6, 2012.

(30) Foreign Application Priority Data

Jun. 6, 2011    (JP) ................................. 2011-126732

(51) Int. Cl.
```
A61B 8/00      (2006.01)
A61B 8/08      (2006.01)
G01S 15/89     (2006.01)
G01S 7/52      (2006.01)
```

(52) U.S. Cl.
CPC .......... *A61B 8/5207* (2013.01); *A61B 8/0891* (2013.01); *A61B 8/463* (2013.01); *A61B 8/488* (2013.01); *A61B 8/5246* (2013.01); *G01S 7/52066* (2013.01); *G01S 7/52073* (2013.01); *G01S 7/52074* (2013.01);
(Continued)

(58) Field of Classification Search
CPC ....... A61B 8/0891; A61B 8/461; A61B 8/463; A61B 8/466; A61B 8/488
See application file for complete search history.

(56) References Cited

U.S. PATENT DOCUMENTS

| | | |
|---|---|---|
| 5,513,640 A | 5/1996 | Yamazaki et al. |
| 5,628,322 A | 5/1997 | Mine |
| 5,664,571 A | 9/1997 | Yamazaki |

(Continued)

FOREIGN PATENT DOCUMENTS

| | | |
|---|---|---|
| CN | 1795397 A | 6/2006 |
| JP | 8-299342 A | 11/1996 |

(Continued)

OTHER PUBLICATIONS

Ararat, Creating multiple y axis graph in excel 2007, http://www.yuvalararat.com/2008/09/creating-multiple-y-axis-graph-in-excel-2007/.*

(Continued)

*Primary Examiner* — Christopher Cook
(74) *Attorney, Agent, or Firm* — Oblon, McClelland, Maier & Neustadt, L.L.P.

(57) ABSTRACT

According to one embodiment, based on a reception signal, the Doppler signal generation unit generates a first Doppler signal attributed to motion of a living body in a ROI and a second Doppler signal attributed to slower motion. The velocity display scale determination unit determines first and second velocity display scales based on velocity distribution ranges for the first and second Doppler signals, respectively. The image generation unit generates first and second Doppler images based on the first and second Doppler signals, respectively. The display unit displays the first and second Doppler images with the first and second velocity display scales, respectively.

11 Claims, 17 Drawing Sheets

(52) U.S. Cl.
CPC ............ G01S 15/8979 (2013.01); *A61B 8/461* (2013.01); *A61B 8/466* (2013.01)

(56) References Cited

U.S. PATENT DOCUMENTS

| | | | |
|---|---|---|---|
| 5,785,657 | A | 7/1998 | Breyer et al. |
| 6,419,632 | B1* | 7/2002 | Shiki ................. A61B 8/06 600/443 |
| 2003/0158484 | A1 | 8/2003 | Pan et al. |
| 2006/0020205 | A1* | 1/2006 | Kamiyama ............ A61B 8/469 600/437 |
| 2006/0074309 | A1* | 4/2006 | Bonnefous ............. A61B 8/483 600/437 |
| 2006/0264754 | A1 | 11/2006 | Frisa et al. |
| 2011/0196237 | A1* | 8/2011 | Pelissier ................. A61B 8/06 600/454 |
| 2011/0218435 | A1* | 9/2011 | Srinivasan ............... A61B 8/06 600/441 |

FOREIGN PATENT DOCUMENTS

| | | |
|---|---|---|
| JP | 9-511411 | 11/1997 |
| JP | 10-216129 A | 8/1998 |
| JP | 2001-161691 A | 6/2001 |
| JP | 2005-102718 A | 4/2005 |
| JP | 2007-502685 A | 2/2007 |
| WO | WO 2011/023797 A1 | 3/2011 |

OTHER PUBLICATIONS

Luo et al., "Imaging of Wall Motion Coupled with Blood Flow Velocity in the Hearts and Vessels in vivo: A feasibility study", published online May 5, 2011, Ultrasound Med. Bio.*
Pellett et al., "The Doppler Velocity Waveform", Echocardiography, vol. 23, Jul. 2006.*
International Search Report and Written Opinion dated Sep. 11, 2012 in PCT/JP2012/064584 with English Translation of Category of Documents.
Office Action dated Feb. 3, 2015 in Japanese Patent Application No. 2011-126732.
International Search Report dated Sep. 11, 2012 in Application No. PCT/JP2012/064584 (Submitting English Translation).
Combined Office Action and Search Report dated Apr. 17, 2014, in Chinese Patent Application No. 201280000541.3 with English translation.
International Search Report and Written Opinion dated Sep. 11, 2012 in PCT/JP2012/064584 with English Translation of Category of Cited Documents.

* cited by examiner

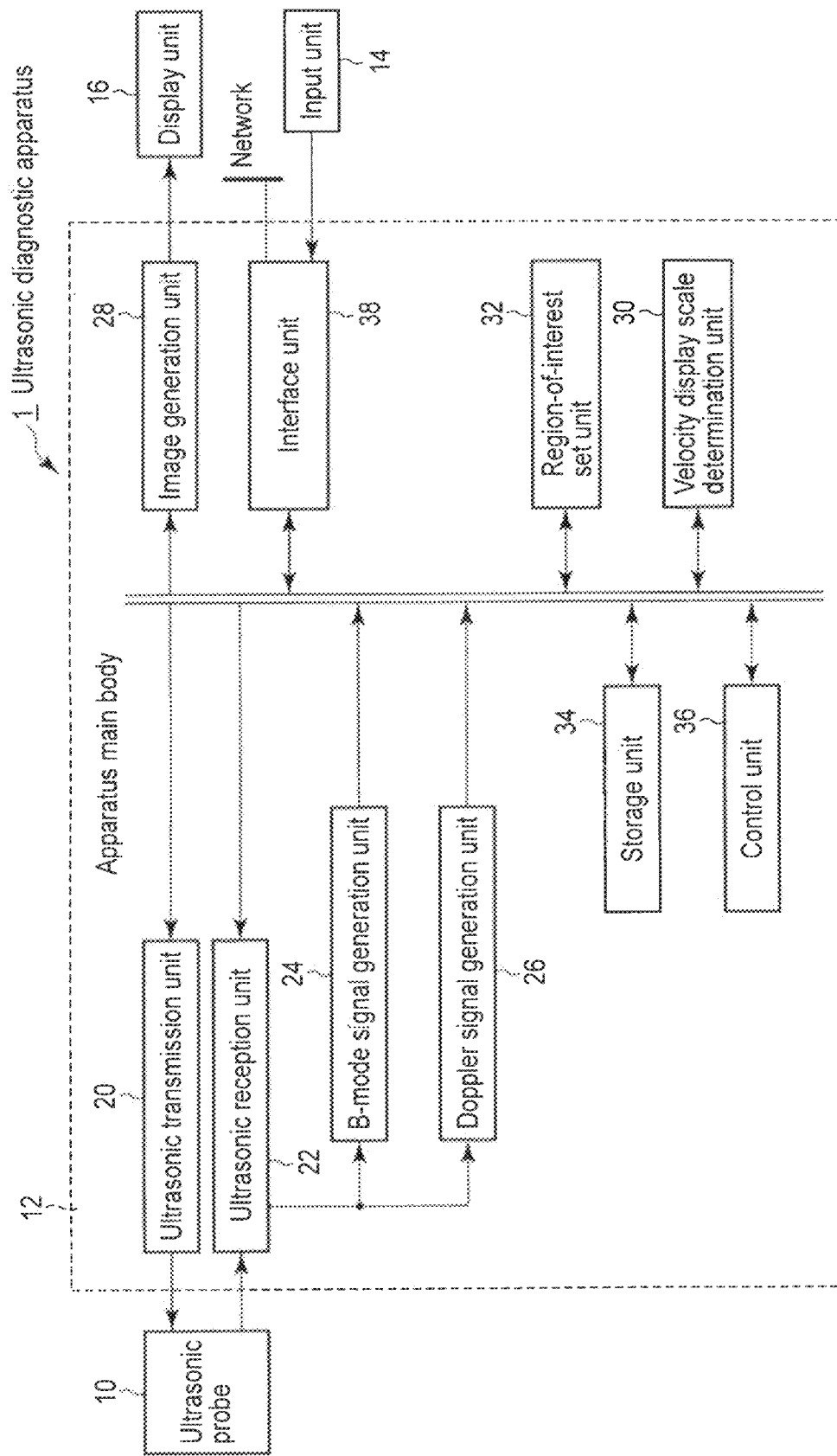
F I G. 1

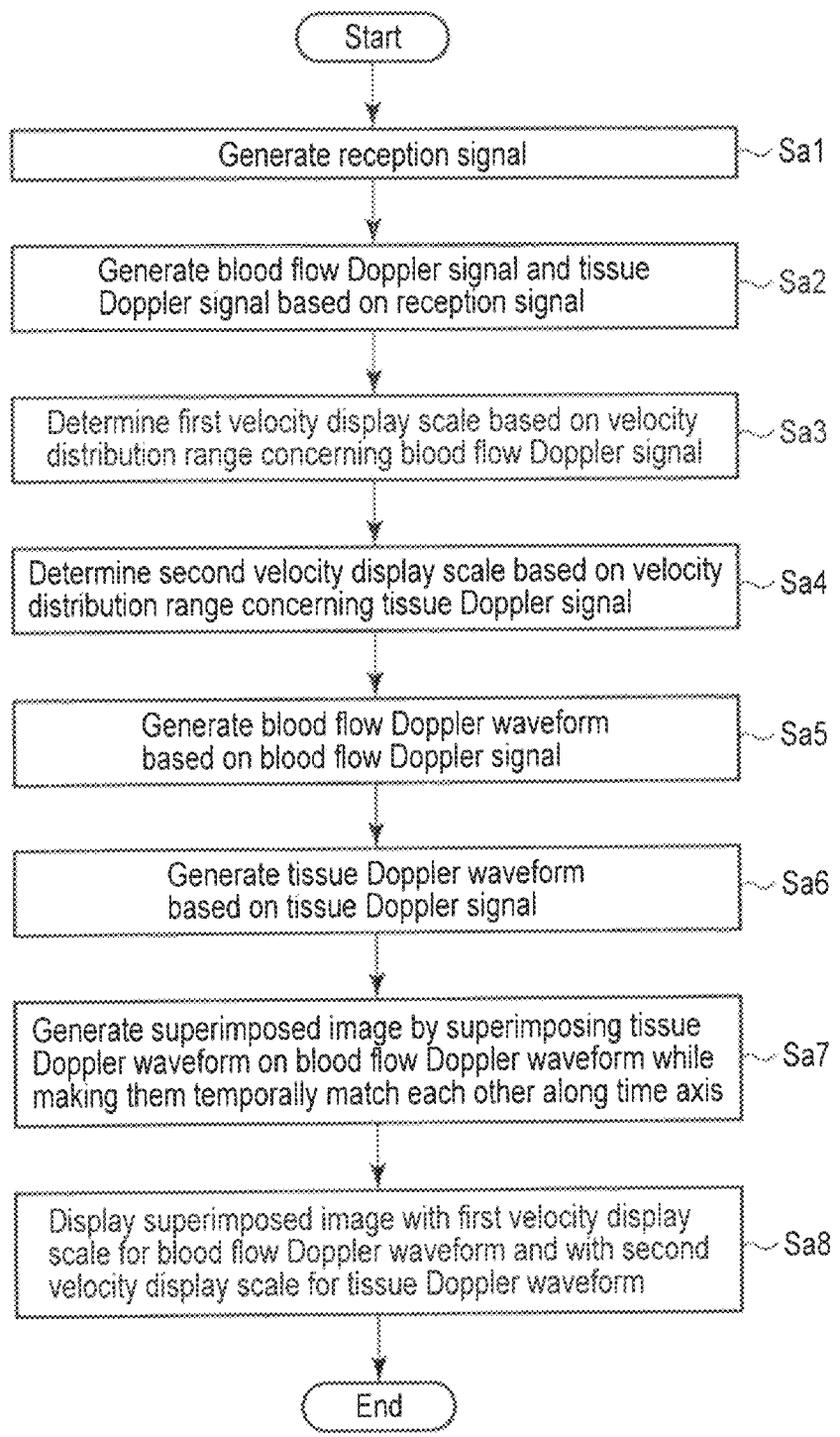
F I G. 3

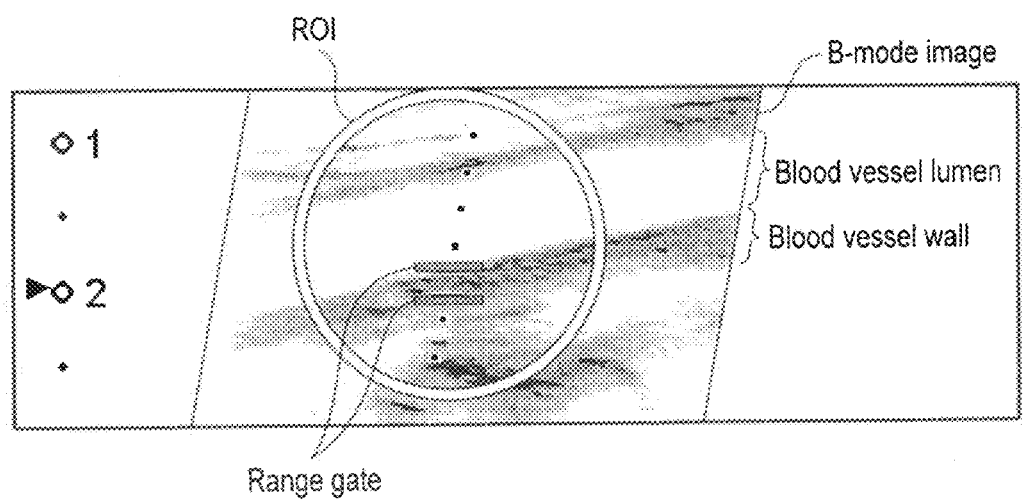
F I G. 4

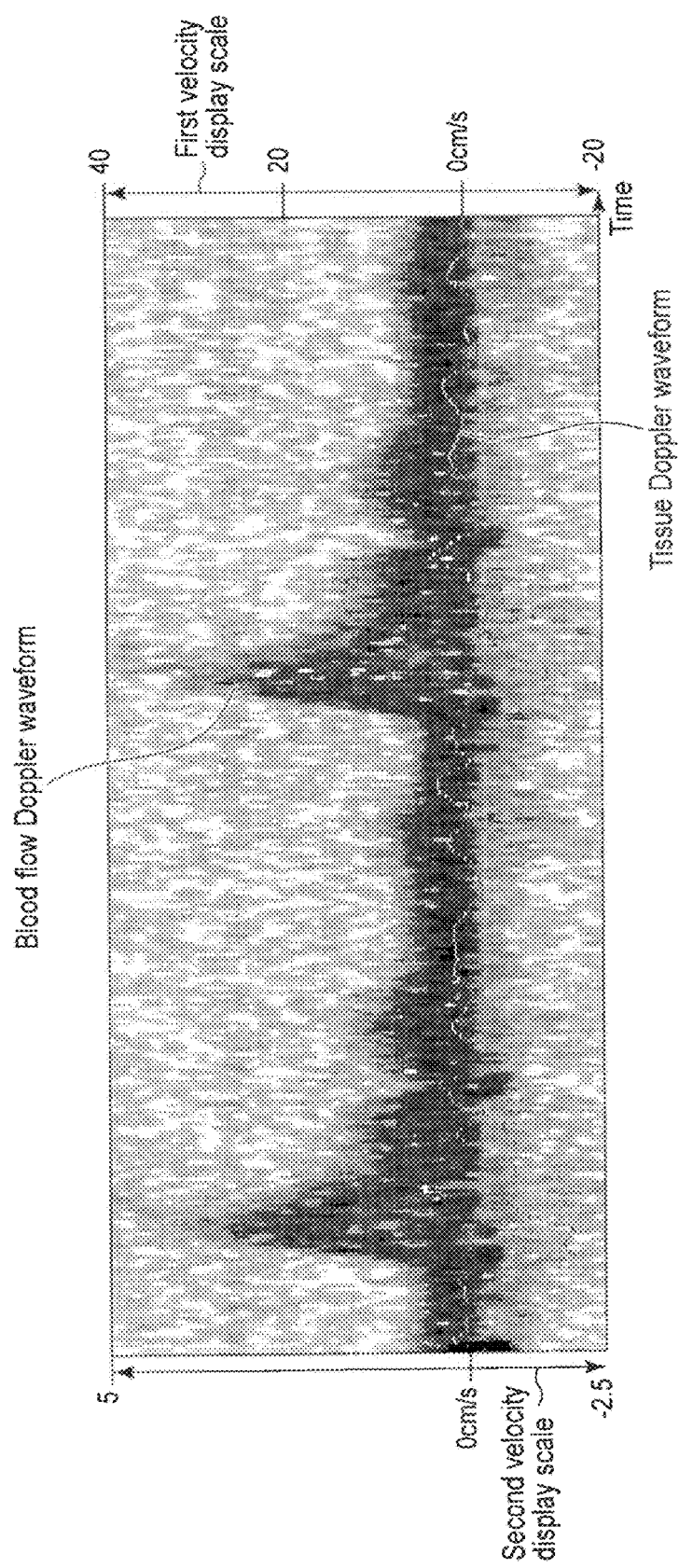
F I G. 5

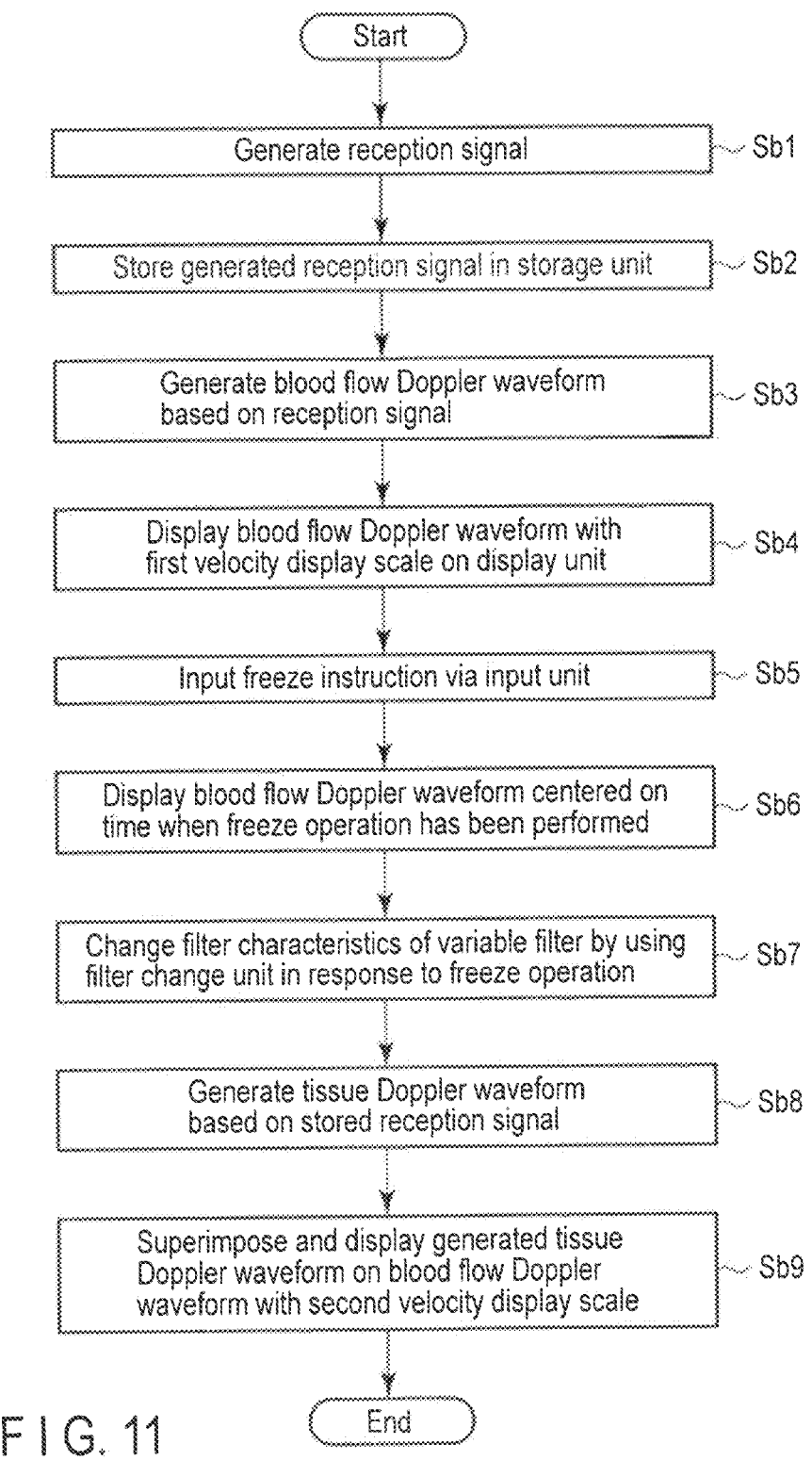
F I G. 11

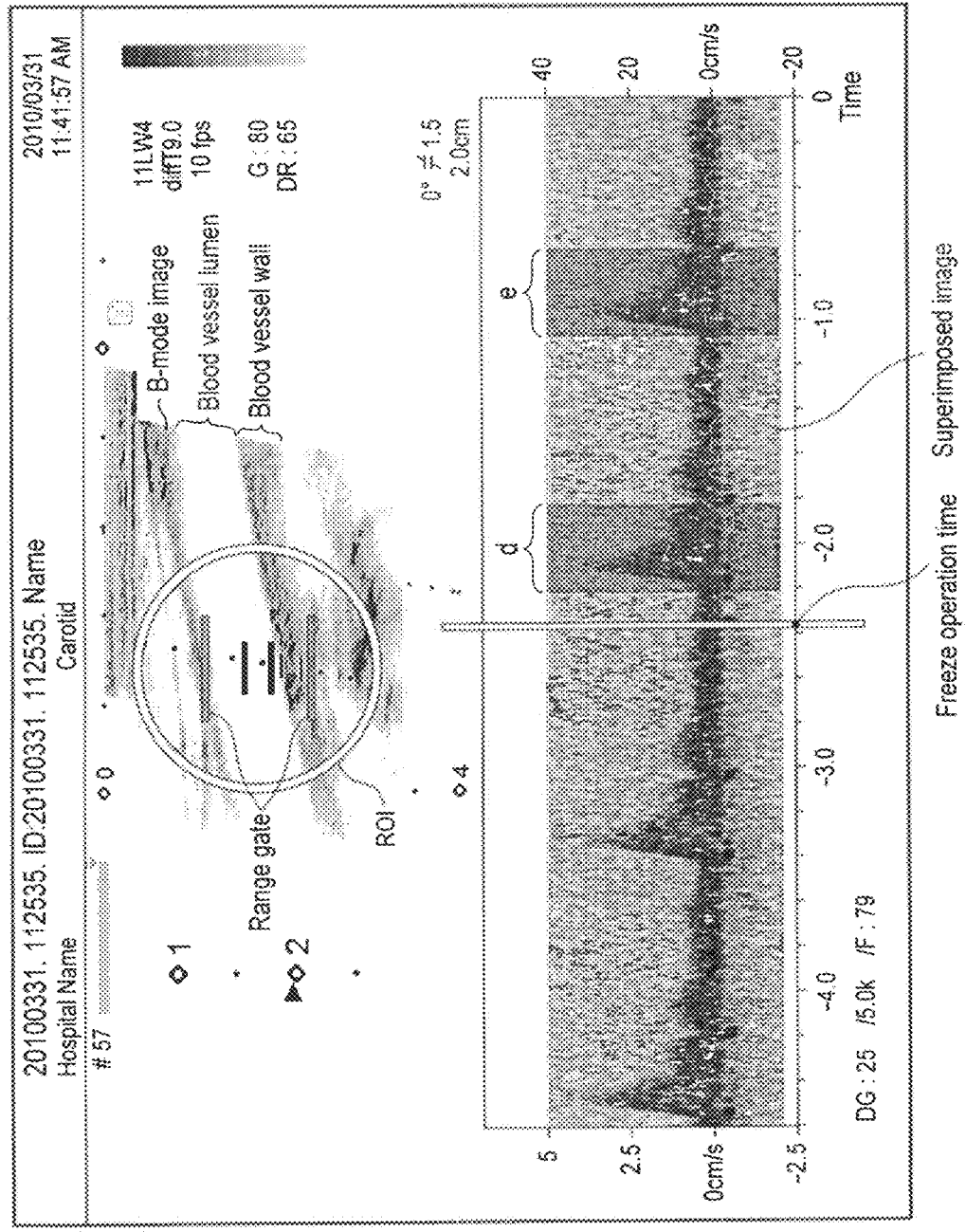
F I G. 13

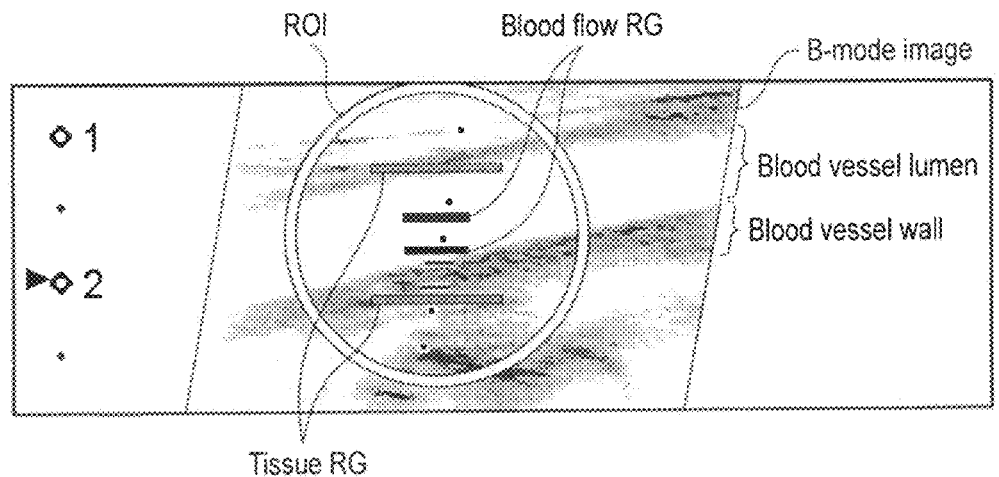
F I G. 15
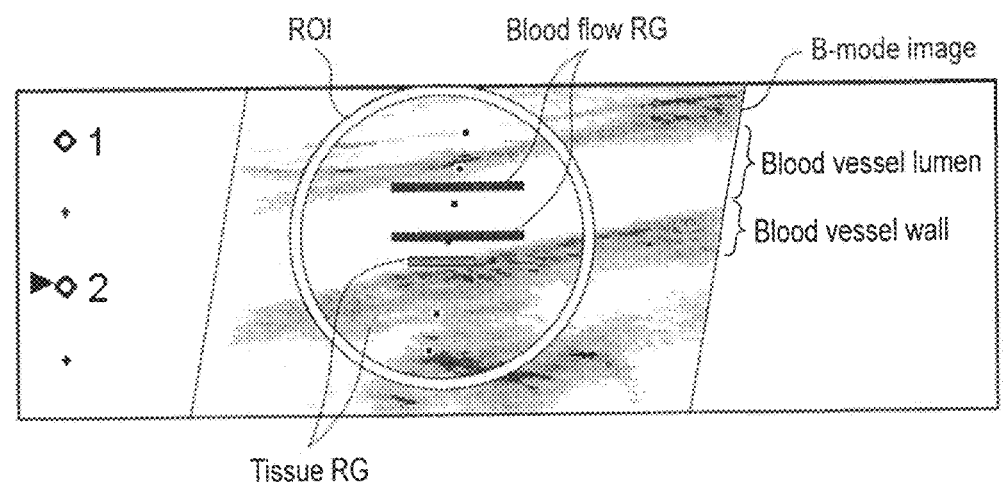
F I G. 16

ULTRASONIC DIAGNOSTIC APPARATUS

CROSS-REFERENCE TO RELATED APPLICATIONS

This application is a Continuation application of PCT Application No. PCT/JP2012/064584, filed Jun. 6, 2012 and based upon and claiming the benefit of priority from Japanese Patent Application No. 2011-126732, filed Jun. 6, 2011, the entire contents of all of which are incorporated herein by reference.

FIELD

Embodiments described herein relate generally to an ultrasonic diagnostic.

BACKGROUND

Conventionally, in order to determine the presence/absence of arteriosclerosis, an ultrasonic diagnostic apparatus sometimes evaluates the phase shift between a blood flow velocity and the motion velocity of a blood vessel wall by a tissue analysis dedicated mode. This apparatus removes unwanted signals mixed in a Doppler signal by filter processing in accordance with the settings of a velocity scale (to be referred to as a velocity display scale hereinafter) to be displayed. A function (to be referred to as a dual Doppler function hereinafter) of displaying pieces of velocity value information concerning different positions in an object which are different azimuth directions in combination with phases displays Doppler signals acquired from different objects in the same velocity display range.

However, the conventional dual Doppler function displays the Doppler signals acquired from different objects within the same velocity display range, and hence it is difficult for the operator to observe displayed images. In addition, since the dual Doppler function is premised on that objects are at different azimuth directions, the function cannot display pieces of velocity value information of different objects in the same azimuth directions in combination with phases. In addition, according to the HPRF (High Pulse Repetition Frequency) method, range gates with different depths are set in one azimuth direction, but only one velocity display range is set. Setting a plurality of range gates is cumbersome operation for the operator, and hence is a heavy load for the operator. Furthermore, it takes much time to perform these operations.

BRIEF DESCRIPTION OF THE DRAWINGS

FIG. 1 is a block diagram showing the arrangement of an ultrasonic diagnostic apparatus according to the first embodiment.

FIG. 3 is a flowchart showing a procedure for the processing of superimposing and displaying a tissue Doppler waveform on a blood flow Doppler waveform with different velocity display scales according to the first embodiment.

FIG. 4 is a view showing an example of a region of interest displayed on a B-mode image according to the first embodiment.

FIG. 5 is a graph showing an example of a superimposed image obtained by superimposing a tissue Doppler waveform on a blood flow Doppler waveform while making them temporally match each other with the respective velocity display scales according to the first embodiment.

FIG. 11 is a flowchart showing a procedure for the processing of changing the filter characteristics of a filter included in a Doppler signal generation unit according to the second embodiment.

FIG. 13 is a view showing an example of a superimposed view obtained by superimposing, on a blood flow Doppler waveform, hues changed in accordance with the intensity values of a tissue Doppler signal after freeze operation and a tissue Doppler waveform after freeze operation while making them temporally match each other with the respective velocity display scales according to the second embodiment.

FIG. 15 is a view showing an example of a plurality of range gates displayed in a region of interest on a B-mode image according to the third embodiment.

FIG. 16 is a view showing an example of a plurality of range gates displayed in a region of interest on a B-mode image according to the third embodiment.

DETAILED DESCRIPTION

Figure 2:
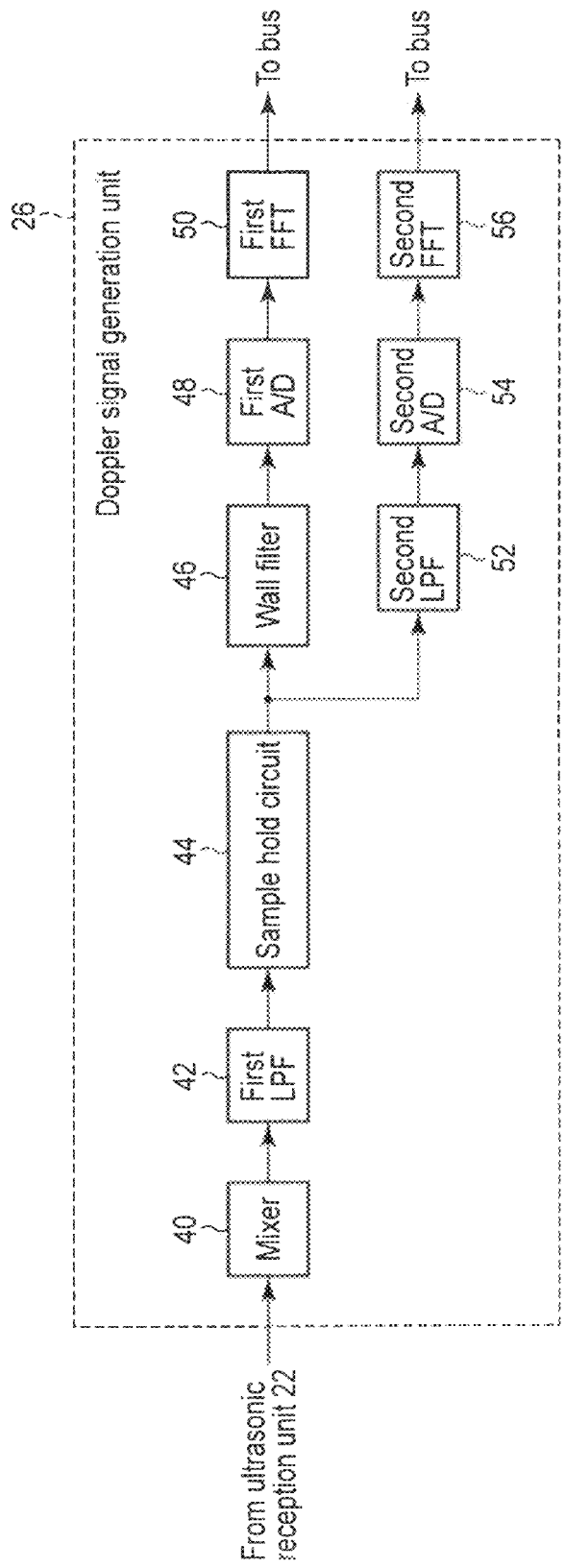
FIG. 2 is a block diagram showing the arrangement of a Doppler signal generation unit in the ultrasonic diagnostic apparatus in FIG. 1 according to the first embodiment.

In general, according to one embodiment, in an ultrasonic diagnostic apparatus includes an ultrasonic probe, an ultrasonic transmission unit, an ultrasonic reception unit, a Doppler signal generation unit, a velocity display scale determination unit, an image generation unit, and a display unit.

The ultrasonic probe is configured to a plurality of transducers. The ultrasonic transmission unit is configured to transmit an ultrasonic wave to an object via the ultrasonic probe. The ultrasonic reception unit is configured to generate a reception signal based on a reflected wave of the ultrasonic wave. The Doppler signal generation unit is configured to generate a first Doppler signal and a second Doppler signal based on the reception signal, wherein the first Doppler signal is attributed to first motion which is motion of a living body in a region of interest in a predetermined azimuth direction, and wherein the second Doppler signal is attributed to second motion slower than the first motion. The velocity display scale determination unit is configured to determine a first velocity display scale based on a velocity distribution range for the first Doppler signal and determine a second velocity display scale based on a velocity distribution range for the second Doppler signal. The image generation unit is configured to generate a first Doppler image based on the first Doppler signal and generate a second Doppler image based on the second Doppler signal. The display unit is configured to display the first Doppler image with the first velocity display scale and display the second Doppler image with the second velocity display scale.

An ultrasonic diagnostic apparatus according to an embodiment will be described below with reference to the accompanying drawing. The same reference numerals denote constituent elements having almost the same arrangements, and a repetitive description will be made only when required.

First Embodiment

FIG. 1 is a block diagram showing the arrangement of an ultrasonic diagnostic apparatus 1 according to the first embodiment. Referring to FIG. 1, the ultrasonic diagnostic apparatus 1 includes an ultrasonic probe 10, an apparatus main body 12, an input unit 14 which is connected to the apparatus main body 12 and serves to input various kinds of instructions, commands, and information from the operator to the apparatus main body 11, and a display unit 16. In addition, a biological signal measurement unit (not shown) typified by an electrocardiograph, phonocardiograph, sphygmograph, or respiration sensor and a network may be connected to the ultrasonic diagnostic apparatus 1 via an interface unit 38.

The ultrasonic probe 10 includes piezoelectric transducers as lossless acoustic/electric conversion elements such as piezoelectric ceramic elements. A plurality of piezoelectric transducers are juxtaposed and mounted on the distal end of the ultrasonic probe 10. Assume that in the following description, one piezoelectric transducer forms one channel.

The apparatus main body 12 includes an ultrasonic transmission unit 20, an ultrasonic reception unit 22, a B-mode signal generation unit 24, a Doppler signal generation unit 26, an image generation unit 28, a velocity display scale determination unit 30, a region-of-interest set unit 32, a storage unit 34, a control unit 36, and an interface unit 38.

The ultrasonic transmission unit 20 includes a pulse generator, a transmission delay circuit, and a pulser (none of which are shown). The pulse generator repetitively generates rate pulses for the formation of transmission ultrasonic waves at a predetermined rate frequency. A pulse generator repetitively generates rate pulses at a predetermined rate frequency of, for example, 5 kHz. These rate pulses are divided for the number of channels used and sent to the transmission delay circuit. The transmission delay circuit gives each rate pulse a delay time necessary to focus an ultrasonic wave into a beam and determine transmission directivity for each channel. Note that the transmission delay circuit receives a trigger as a timing signal from a trigger signal generator (not shown). The pulser applies a voltage pulse to each transducer of the ultrasonic probe 10 at the timing of the reception of a rate pulse from the transmission delay circuit, thereby transmitting ultrasonic beams to the object.

Note that the ultrasonic transmission unit 20 may transmit ultrasonic waves under predetermined transmission conditions corresponding to the blood flow velocity desired by the operator under the control of the control unit 36 (to be described later). The predetermined transmission conditions include, for example, the maximum detection speed of a blood flow, a Doppler angle, the transmission frequency of an ultrasonic wave which corresponds to the maximum detection depth, and a pulse repetition frequency (to be referred to as a PRF hereinafter). The ultrasonic transmission unit 20 may also transmit ultrasonic waves under predetermined transmission conditions corresponding to the motion velocity of a tissue desired by the operator under the control of the control unit 36 (to be described later). The predetermined transmission conditions include, for example, the maximum detection speed of the motion velocity of a tissue, a Doppler angle, the transmission frequency of an ultrasonic wave which corresponds to the maximum detection depth, and a PRF. For example, the transmission frequency of an ultrasonic wave which corresponds to the motion velocity of a tissue is higher than that corresponding to the blood flow velocity.

The ultrasonic reception unit 22 includes a preamplifier, a reception delay circuit, and an adder (none of which are shown). The preamplifier circuit amplifies an echo signal received from the object via the ultrasonic probe 10 for each channel. The reception delay circuit gives the echo signals converted into digital signals delay times required to determine reception directivity. The adder adds a plurality of echo signals in accordance with a reception delay pattern from the control unit 36 (to be described later). This addition enhances a reflection component from a direction corresponding to the reception directivity. The transmission directivity and the reception directivity determine the overall directivity of ultrasonic transmission/reception. This directivity determines a so-called ultrasonic scanning line. The ultrasonic reception unit 22 generates a reception signal corresponding to the ultrasonic wave transmitted from the ultrasonic transmission unit 20. Note that the ultrasonic reception unit 22 may have a parallel reception function of simultaneously receiving echo signals generated on a plurality of scanning lines by one ultrasonic transmission.

Note that the ultrasonic reception unit 22 may receive ultrasonic waves under predetermined reception conditions corresponding to the blood flow velocity desired by the operator under the control of the control unit 36 (to be described later). The predetermined reception conditions include, for example, the maximum detection speed of a blood flow, a Doppler angle, the transmission frequency of an ultrasonic wave which corresponds to the maximum detection depth, and a PRF. For example, the reception condition is the reception center frequency. The ultrasonic reception unit 22 can also receive ultrasonic waves under predetermined reception conditions corresponding to the motion velocity of a tissue desired by the operator under the control of the control unit 36 (to be described later). The predetermined reception conditions include, for example, the maximum detection speed of the motion velocity of a tissue, a Doppler angle, the transmission frequency of an ultrasonic wave which corresponds to the maximum detection depth, and a PRF. For example, the reception condition is the reception center frequency. For example, the reception center frequency which corresponds to the motion velocity of a tissue is higher than that of an ultrasonic wave corresponding to the blood flow velocity.

The B-mode signal generation unit 24 includes an envelope detector, a logarithmic converter, and an analog/digital converter (none of which are shown). The envelope detector executes envelope detection of an input signal to the B-mode signal generation unit 24, i.e., the reception signal output from the ultrasonic reception unit 22. The logarithmic converter relatively enhances a weak signal by logarithmically converting the amplitude of the detected signal. The analog/digital converter converts the output signal from this logarithmic converter to generate a B-mode signal. The B-mode signal generation unit 24 outputs the generated B-mode signal to the image generation unit 28.

The Doppler signal generation unit 26 will be described with reference to FIG. 2. FIG. 2 is a block diagram showing the arrangement of the Doppler signal generation unit 26 in the ultrasonic diagnostic apparatus 1. The Doppler signal generation unit 26 includes a mixer 40, a first low-pass filter (to be referred to as a first LPF hereinafter) 42, a sample hold (to be referred to as an SH hereinafter) circuit 44, a wall filter 46, a first analog/digital converter (to be referred to as a first A/D hereinafter) 48, a first frequency analyzer (Fast Fourier Transform (to be referred to as a first FFT hereinafter) 50, a second low-pass filter (to be referred to as a second LPF hereinafter) 52, a second analog/digital converter (to be referred to as a second A/D hereinafter) 54, and a second frequency analyzer (Fast Fourier Transform to be referred to as a second FFT hereinafter) 56.

The mixer 40 multiplies the signal output from the ultrasonic reception unit 22 by a reference signal having a frequency f0 equal to the transmission frequency. This multiplication yields a signal having a Doppler shift frequency fd (to be referred to as a Doppler signal hereinafter) and a signal having a frequency component (2f0+fd). The first LPF 42 removes the signal having the high frequency component (2f0+fd) from the signal having the two types of frequency components.

The SH circuit 44 samples and holds part of a Doppler signal in accordance with a sampling pulse from a range gate circuit (not shown). The range gate circuit generates a sampling pulse with a predetermined pulse width at a timing delayed from a rate pulse by a predetermined delay time. The predetermined delay time is the time taken for an ultrasonic wave to reciprocally propagate the distance between a piezoelectric transducer and the range gate (also called a sampling point or sampling volume) set at the depth desired by the operator. The region-of-interest set unit 32 (to be described later) sets a range gate in accordance with an instruction from the operator via the input unit 14 (to be described later). A range gate is provided in a region of interest (to be referred to as an ROI hereinafter) set on the B-mode image displayed on the display unit 16 (to be described later).

Note that a sampling pulse time interval (to be referred to as a sampling interval hereinafter) may be set in accordance with a blood flow velocity and the motion velocity of a tissue. Alternatively, a sampling interval may be set based on the velocity display scale determined by the velocity display scale determination unit 30. For example, a sampling interval corresponding to the motion velocity of a tissue is set to be shorter than a sampling interval corresponding to a blood flow velocity because the motion velocity of the tissue is lower than the blood flow velocity.

The wall filter 46 removes a second Doppler signal (to be referred to as a tissue Doppler signal hereinafter) corresponding to a velocity attributed to the motion of a blood vessel wall, cardiac valve, or the like from an output from the SH circuit 44 to extract a first Doppler signal (to be referred to as a blood flow Doppler signal hereinafter) attributed to a blood flow. The wall filter 46 outputs a blood flow Doppler signal to the first A/D 48. The first A/D 48 converts the blood flow Doppler signal to a digital signal.

The first FFT 50 executes frequency analysis of the blood flow Doppler signal converted into the digital signal by fast Fourier transform. The first FFT 50 generates the frequency spectrum of the blood flow Doppler signal based on the frequency analysis result. The first FFT 50 outputs the frequency spectrum of the blood flow Doppler signal (to be referred to as a blood flow Doppler spectrum hereinafter) to the image generation unit 28 (to be described later) and the velocity display scale determination unit 30 (to be described later). The blood flow Doppler spectrum indicates the frequency of the blood flow Doppler signal and the intensity of the frequency in association with the time. The frequency of the blood flow Doppler signal corresponds to the blood flow velocity.

Note that a sample count (to be referred to as the first sample count hereinafter) in fast Fourier transform by the first FFT 50 may be set in accordance with a blood flow velocity. The first sample count may also be determined based on the velocity display scale determined by the velocity display scale determination unit 30 (to be described later).

The second LPF 52 removes the blood flow Doppler signal from the output from the SH circuit 44 to extract a tissue Doppler signal. The second LPF 52 outputs the tissue Doppler signal to the second A/D 54. The second A/D 54 converts the tissue Doppler signal to a digital signal. The second FFT 56 executes frequency analysis of the tissue Doppler signal which has been converted into a digital signal by fast Fourier transform.

The second FFT 56 generates the frequency spectrum of the tissue Doppler signal based on the frequency analysis result. The second FFT 56 outputs the frequency spectrum of the tissue Doppler signal (to be referred to as a tissue Doppler spectrum hereinafter) to the image generation unit 28 (to be described later) and the velocity display scale determination unit 30 (to be described later). The tissue Doppler spectrum indicates the frequency of the tissue Doppler signal and the intensity of the frequency as a function of time. The frequency of the tissue Doppler signal corresponds to the motion velocity of the tissue. For the sake of simplicity, assume that the motion velocity of the tissue is the motion velocity of the blood vessel wall.

Note that a sample count (to be referred to as the second sample count hereinafter) in fast Fourier transform by the second FFT 56 may be set in accordance with the motion velocity of a tissue. The second sample count may also be determined based on the velocity display scale determined by the velocity display scale determination unit 30 (to be described later). For example, the second sample count is set to be larger than the first sample count because the motion velocity of a tissue is lower than the blood vessel velocity.

Note that when generating a Doppler signal from a reception signal, it is also possible to generate the center of a Doppler spectrum (i.e., a central velocity), power, variance value, and the like by using an autocorrelation function and the like instead of frequency analysis by FFT like that described above.

The image generation unit 28 maps B-mode signals in a dedicated memory in accordance with position information (mapping processing). The image generation unit 28 then interpolates B-mode signals between ultrasonic scanning lines (interpolation processing). The image generation unit 28 generates a B-mode image constituted by a plurality of pixels by mapping processing and interpolation processing. Each pixel has a pixel value corresponding to the intensity (amplitude) of a corresponding B-mode signal.

Note that the image generation unit 28 may have a volume data generating device (not shown). At this time, the volume data generating device maps the B-mode signals output from the B-mode signal generation unit 24 in a dedicated memory in accordance with position information (mapping processing). Subsequently, the volume data generating device interpolates B-mode signals between ultrasonic scanning lines (interpolation processing). Mapping processing and interpolation processing generate volume data constituted by a plurality of voxel data. Each voxel has a voxel value corresponding to the intensity of a corresponding B-mode signal. The generated volume data will undergo rendering processing by a three-dimensional image data generating device (not shown). The volume data having undergone rendering processing is output to the display unit 16.

The image generation unit 28 generates a blood flow Doppler image based on the blood flow Doppler spectrum output from the Doppler signal generation unit 26. A blood flow Doppler image is an image indicating a waveform (to be referred to as a blood flow Doppler waveform hereinafter) representing the signal intensities of a blood flow Doppler signal as the magnitudes of luminances or pixel values, with the ordinate representing the Doppler shift frequency attributed to a blood flow and the abscissa representing the time.

The image generation unit 28 generates a tissue Doppler image based on the tissue Doppler spectrum output from the Doppler signal generation unit 26. A tissue Doppler image is an image indicating a waveform (to be referred to as a tissue Doppler waveform hereinafter) representing the signal intensities of a tissue Doppler signal as the magnitudes of luminances or pixel values, with the ordinate representing the Doppler shift frequency attributed to a tissue (e.g., a blood vessel wall) and the abscissa representing the time.

The image generation unit 28 has a frame memory or the like (not shown). The image generation unit 28 combines character information, scale marks, or the like of various kinds of parameters on a B-mode image, blood flow Doppler waveform, and tissue Doppler waveform. The image generation unit 28 outputs the combined image to the display unit 16. The image generation unit 28 generates an image (to be referred to as a superimposed image hereinafter) by superimposing a tissue Doppler waveform on a blood flow Doppler waveform while making them temporally match each other along the time axis. Note that the image generation unit 28 may generate a combined image by combining a superimposed image with a B-mode image. A B-mode image, blood flow Doppler waveform, and tissue Doppler waveform will be referred to as ultrasonic images hereinafter.

Based on a velocity distribution range (to be referred to as the first velocity distribution range hereinafter) concerning the blood flow Doppler signal generated by the Doppler signal generation unit 26, the velocity display scale determination unit 30 determines the first velocity display scale to include the first velocity distribution range. The first velocity distribution range is, for example, a velocity display scale for the blood flow velocities estimated from the types of blood vessels and the like. Based on a velocity distribution range (to be referred to as the second velocity distribution range hereinafter) concerning the tissue Doppler signal generated by the Doppler signal generation unit 26, the velocity display scale determination unit 30 determines the second velocity display scale to include the second velocity distribution range. The second velocity distribution range is, for example, a velocity display scale for the motion velocities of a blood vessel wall estimated from the types of blood vessels and the like. Note that the first and second velocity display scales can be adjusted, as needed, in accordance with instructions from the operator via the input unit 14 (to be described later).

In addition, the velocity display scale determination unit 30 may determine the first velocity display scale based on the first value stored in the storage unit 34. The first value is, for example, the maximum possible value of blood flow velocities. Note that the first value can be changed, as needed, by an instruction from the operator via the input unit 14 (to be described above). The velocity display scale determination unit 30 may determine the second velocity display scale based on the second value stored in the storage unit 34. The second value is, for example, the maximum possible value of the motion velocities of a tissue. Note that the second value can be changed, as needed, in accordance with an instruction from the operator via the input unit 14 (to be described later). A memory (not shown) in the velocity display scale determination unit 30 may store the first and second values.

Since motion velocities of blood vessel walls accompanying expansion and contraction are generally lower than blood flow velocities, the velocity display scale determination unit 30 may determine, as the second velocity display scale, a velocity display scale larger than the first velocity display scale. For example, the velocity display scale determination unit 30 determines, as the second velocity display scale, a scale obtained by multiplying the first velocity display scale by a predetermined ratio. In this case, the predetermined ratio is the maximum value of the motion velocities of a tissue relative to the maximum possible value of blood flow velocities. The predetermined ratio will be referred to as a velocity ratio hereinafter. If, for example, the velocity ratio is 1/8 and the first velocity display scale ranges from −20 cm/sec to 40 cm/sec, the second velocity display scale ranges from −2.5 cm/sec to 5 cm/sec. The storage unit 34 (to be described later) stores the velocity ratio. Note that a memory (not shown) in the velocity display scale determination unit 30 may store the velocity ratio. Note that the operator can change the velocity ratio via the input unit 14, as needed.

The velocity display scale determination unit 30 may determine, as the first velocity display scale, a velocity display scale smaller than the second velocity display scale. For example, the velocity display scale determination unit 30 determines, as the first velocity display scale, a scale obtained by multiplying the second velocity display scale by the reciprocal of the velocity ratio described above. If, for example, the reciprocal of the velocity ratio is 8 and the second velocity display scale ranges from −2.5 cm/sec to 5 cm/sec, the first velocity display scale ranges from −20 cm/sec to 40 cm/sec.

Note that the velocity display scale determination unit 30 may determine the first velocity display scale based on the maximum value of the blood flow velocities on the blood flow Doppler spectrum in a predetermined interval which is output from the Doppler signal generation unit 26. The velocity display scale determination unit 30 may also determine the second velocity display scale based on the maximum value of the motion of a tissue on the tissue Doppler spectrum in a predetermined interval which is output from the Doppler signal generation unit 26. The predetermined interval is, for example, one or a plurality of cardiac cycles. Note that it is possible to change the predetermined interval via the input unit 14 (to be described later), as needed.

The region-of-interest set unit 32 sets an ROI on the B-mode image displayed on the display unit 16 in accordance with an instruction input by the operator via the input unit 14. The region-of-interest set unit 32 sets a range gate in the ROI in accordance with an instruction input by the operator via the input unit 14. The region-of-interest set unit 32 outputs a delay time corresponding to the set range gate to the range gate circuit of the SH circuit 44.

The storage unit 34 stores a plurality of reception delay patterns with different focus depths, control programs for the ultrasonic diagnostic apparatus 1, a diagnostic protocol, various kinds of data such as transmission/reception conditions, the B-mode signals generated by the B-mode signal generation unit 24, the blood flow Doppler spectra and tissue Doppler spectra generated by the Doppler signal generation unit 26, ultrasonic images such B-mode images, blood flow Doppler waveforms, and tissue Doppler waveforms generated by the image generation unit 28, the first and second values, velocity ratios, and the like. Note that the storage unit 34 may store a correspondence table between the first and second velocity display scales and ultrasonic transmission/reception conditions.

The control unit 36 reads out transmission/reception conditions and apparatus control programs stored in the storage unit 34 based on the mode selection, ROI setting, first and second velocity display scales, reception delay pattern list selection, and transmission start/end instructions, which are input by the operator via the input unit 14. The ultrasonic diagnostic apparatus 1 performs control in accordance with these inputs.

The interface unit 38 is an interface concerning the input unit 14, network, external storage device (not shown), and biological signal measurement unit (not shown). It is possible to transfer data such as ultrasonic images, analysis results, and the like obtained by the ultrasonic diagnostic apparatus 1 to other devices such as the interface unit 38 and the network.

The input unit 14 is connected to the interface unit 38 and inputs various kinds of instruction, commands, information, selections, and settings from the operator to the ultrasonic diagnostic apparatus 1. The input unit 14 includes input devices such as a trackball, switch buttons, mouse, and keyboard (not shown). The input device detects the coordinates of a cursor displayed on the display screen, and outputs the detected coordinates to the control unit 36. Note that the input device may be a touch panel provided to cover the display screen. In this case, the input unit 14 detects touched and designated coordinates by a coordinate reading principle such as an electromagnetic induction scheme, magnetostriction scheme, or a pressure-sensitive scheme, and outputs the detected coordinates to the control unit 36. When, for example, the operator operates the end button or FREEZE button of the input device 14, the transmission/reception of ultrasonic waves is terminated, and the ultrasonic diagnostic apparatus 1 is set in a pause state. The input unit 14 inputs a slice position, a display format, a ray direction in rendering processing, and the like in association with the volume data of an object transferred from another medical image diagnostic apparatus via the interface unit 38. Note that the input unit 14 inputs the first and second velocity display scales, first and second values, velocity ratio, predetermined interval, range gate, and the like to the ultrasonic diagnostic apparatus 1.

The display unit 16 displays the B-mode image output from the image generation unit 28. The display unit 16 displays the blood flow Doppler waveform generated by the image generation unit 28 with the first velocity display scale. The display unit 16 displays the tissue Doppler waveform generated by the image generation unit 28 with the second velocity display scale. The display unit 16 displays the superimposed image generated by the image generation unit 28. The superimposed image is displayed with the first velocity display scale for the blood flow Doppler waveform, and is displayed with the second velocity display scale for the tissue Doppler waveform. The display unit 16 displays the combined image generated by the image generation unit 28. The display unit 16 can also display a rendering image or the like which is input from another medical image diagnostic apparatus via the interface unit 38.

(Velocity Display Scale Determination Function)

A velocity display scale determination function is a function of determining the first velocity display scale based on a velocity distribution range concerning a blood flow Doppler signal and determining the second velocity display scale based on a velocity distribution range concerning a tissue Doppler signal. Processing based on the velocity display scale determination function (to be referred to as velocity display scale determination processing hereinafter) will be described below.

FIG. 3 is a flowchart showing a procedure for velocity display scale determination processing.

The ultrasonic reception unit 22 generates a reception signal (step Sa1). The apparatus generates a blood flow Doppler signal and a tissue Doppler signal based on the generated reception signal (step Sa2). The apparatus determines the first velocity display scale based on a velocity distribution range concerning the blood flow Doppler signal (step Sa3). The apparatus determines the second velocity display scale based on a velocity distribution range concerning the tissue Doppler signal (step Sa4). Note that the second velocity display scale may be determined by multiplying the first velocity display scale by a velocity ratio. The apparatus generates a blood flow Doppler waveform based on the blood flow Doppler signal (step Sa5). The apparatus generates a tissue Doppler waveform based on the tissue Doppler signal (step Sa6). The apparatus generates a superimposed image of the blood flow Doppler waveform and the tissue Doppler waveform while making them temporally match each other along the time axis (step Sa7). The display unit 16 displays the generated superimposed image with the first velocity display scale for the blood flow waveform, and with the second velocity display scale for the tissue Doppler waveform (step Sa8).

FIG. 4 is a view showing an example of the ROI set on the B-mode image displayed on the display unit 16. A range gate is set in the ROI. The range gate in FIG. 4 is set on the blood vessel wall. When this embodiment is applied to this technique, the range gate is adjusted in accordance with an instruction from the operator via the input unit 14 so as to include the lumen of a blood vessel (to be referred to as a blood vessel lumen hereinafter) and a blood vessel wall.

Figure 6:
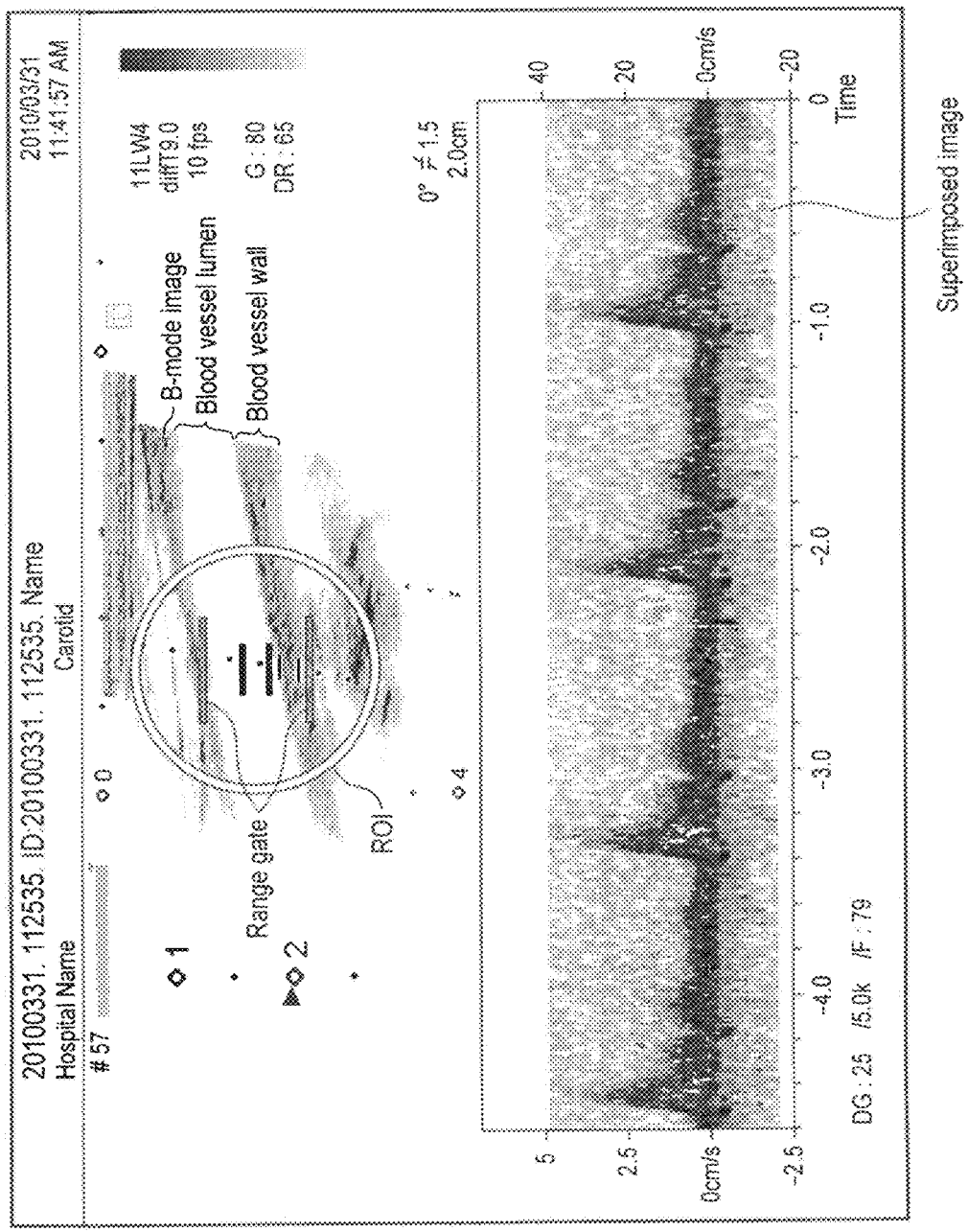
FIG. 6 is a view showing an example of a display window including the images in FIGS. 4 and 5 according to the first embodiment.

FIG. 5 is a view showing an example of a superimposed image by superimposing a tissue Doppler waveform (dotted line) on a blood vessel Doppler waveform while making them temporally match each other along the time axis. Referring to FIG. 5, the ordinate represents the blood flow velocity and the motion velocity of the tissue, and the abscissa represents time. The blood vessel Doppler waveform in FIG. 5 is displayed with the first velocity display scale. The ordinate on the right side of the superimposed image in FIG. 5 is an axis representing the velocity concerning the blood flow Doppler waveform. The ordinate on the left side of the superimposed image in FIG. 6 is an axis representing the velocity concerning the tissue Doppler waveform. The upper limit of the first velocity display scale is 40 cm/s. The tissue Doppler waveform in FIG. 5 is displayed with the second velocity display scale. The upper limit of the second velocity display scale is 5 cm/s.

FIG. 6 is a view showing an example of the combined image displayed on the display unit 16. The ROI set in accordance with an instruction from the operator via the input unit 14 is displayed on the B-mode image in FIG. 6. The range gate set in accordance with the instruction from the operator via the input unit 14 is displayed in the ROI. Note that the range gate includes the blood vessel lumen and the blood vessel wall. The ordinate on the right side of the superimposed image in FIG. 6 is an axis representing the velocity concerning the blood flow Doppler waveform. The ordinate on the left side of the superimposed image in FIG. 6 is an axis representing the velocity concerning the tissue Doppler waveform.

(Modification)

This modification differs from the first embodiment in that it changes the hue of the background of a tissue Doppler waveform on a tissue Doppler image to a predetermined hue based on the tissue Doppler spectrum. More specifically, this modification changes the hue of the background of the tissue Doppler waveform to a predetermined hue based on the frequency of the tissue Doppler spectrum. Note that the apparatus may change the hue of the background of the tissue Doppler waveform to a predetermined hue based on the frequency intensity on the tissue Doppler spectrum.

Note that it is possible to change the luminance of the background of a tissue Doppler waveform on a tissue Doppler image to a predetermined luminance based on the tissue Doppler spectrum. More specifically, the luminance of the background of the tissue Doppler waveform is changed to a predetermined luminance based on the frequency of the tissue Doppler spectrum. Note that it is possible to change the luminance of the background of the tissue Doppler waveform to a predetermined luminance based on the frequency intensity on the tissue Doppler spectrum.

For the sake of simplicity, assume that the hue of the background of a tissue Doppler waveform is changed.

The storage unit 34 stores a threshold concerning whether to change a hue. The threshold to be stored is, for example, a predetermined frequency (to be referred to as a threshold frequency hereinafter) concerning a tissue Doppler spectrum or a predetermined frequency intensity (to be referred to as a threshold intensity hereinafter) on a tissue Doppler spectrum. Note that the storage unit 34 may store a plurality of thresholds for changing the hue of the background of a tissue Doppler waveform to a plurality of hues. The storage unit 34 stores target hues. Note that the storage unit 34 may store a plurality of hues. In addition, the storage unit 34 may store target luminances. For the sake of simplicity, assume that the storage unit 34 stores one threshold.

The image generation unit 28 stores, in a memory (not shown), an interval in which the frequency of a tissue Doppler spectrum exceeds a threshold frequency. The image generation unit 28 changes the hue of the background of the tissue Doppler waveform corresponding to the stored interval to a predetermined hue. The image generation unit 28 generates a tissue Doppler image representing a tissue Doppler waveform whose background hue has been changed. The image generation unit 28 outputs the generated tissue Doppler image to the display unit 16. Note that if the threshold stored in the storage unit 34 is a threshold intensity, the image generation unit 28 may store, in a memory (not shown), an interval in which the intensity of a frequency on the tissue Doppler spectrum exceeds a threshold intensity.

Figure 7:
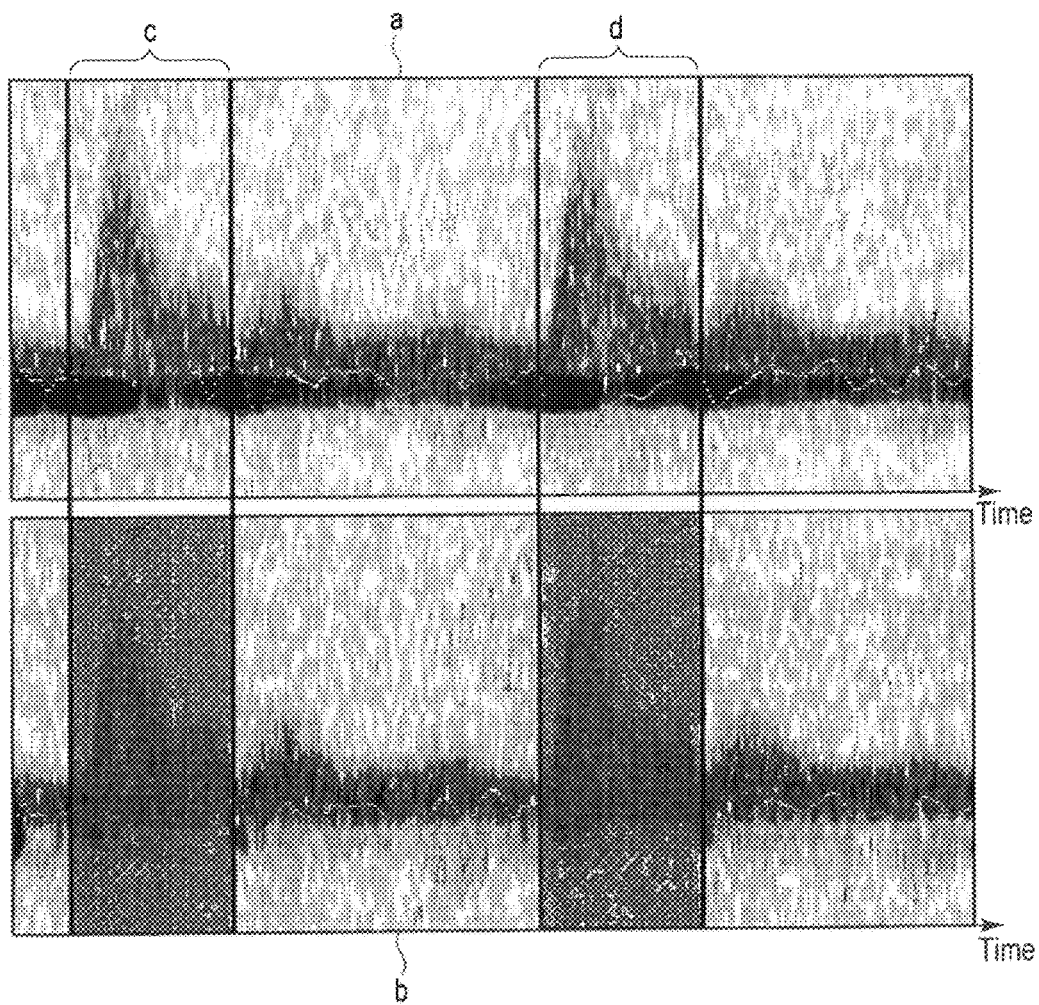
FIG. 7 is a view showing an example of a superimposed image obtained by superimposing, on a blood flow Doppler image, a tissue Doppler image whose hues have been changed in accordance with the velocity values of a tissue Doppler waveform while making them temporally match each other with the respective velocity display scales according to a modification of the first embodiment.

An image a in FIG. 7 is a superimposed image before hue change. A image b in FIG. 7 is a superimposed image after hue change. Regions c and d in FIG. 7 correspond to intervals in which frequencies of the tissue Doppler spectrum exceed a threshold frequency.

Figure 8:
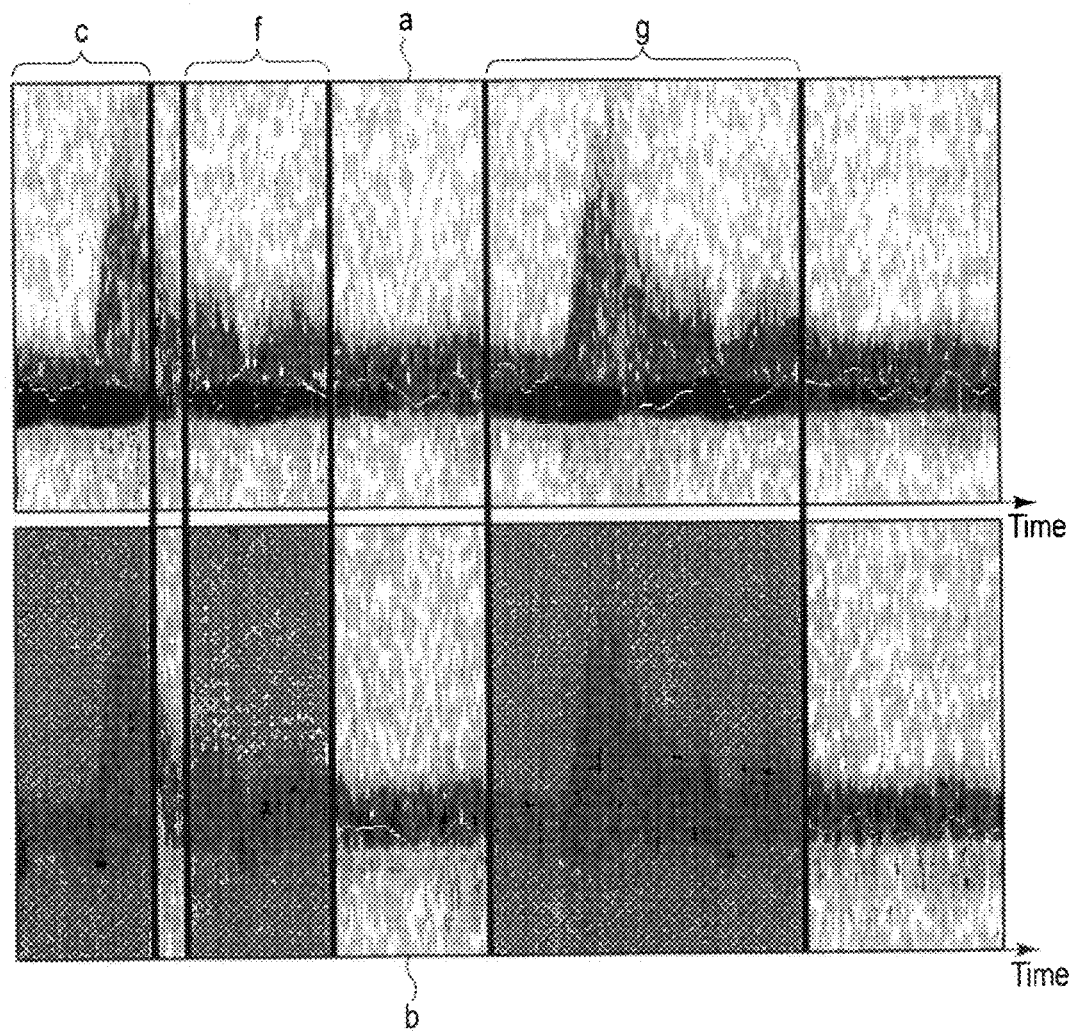
FIG. 8 is a view showing an example of a superimposed image obtained by superimposing, on a blood flow Doppler image, a tissue Doppler image whose hues have been changed in accordance with the intensity values of a tissue Doppler spectrum while making them temporally match each other with the respective velocity display scales according to a modification of the first embodiment.

FIG. 8 is a view showing a superimposed image before hue change. An image a in FIG. 8 is a superimposed image before hue change. A image b in FIG. 8 is a superimposed image after hue change. Regions e, f, and g in FIG. 8 correspond to intervals in which frequency intensities on the tissue Doppler spectrum exceed a threshold intensity.

According to the above arrangement, the following effects can be obtained.

The ultrasonic diagnostic apparatus 1 can superimpose and display a blood flow Doppler waveform and a tissue Doppler waveform with the first and second velocity display scales respectively corresponding to blood flow velocities and the motion velocities of a tissue (e.g., a blood vessel wall). The apparatus can also change the hue or luminance of the background of a tissue Doppler image in accordance with the frequency or frequency intensity on a tissue Doppler waveform. These features allow the operator to easily observe displayed images. In addition, the ultrasonic diagnostic apparatus 1 can generate a blood flow Doppler signal and a tissue Doppler signal by using a reception signal in an ROI in one azimuth direction. This makes it possible to simultaneously observe, for example, the velocity of a blood flow and the motion of a blood vessel wall accompanying the blood flow without setting a plurality of range gates. In addition, it is possible to set transmission/reception conditions, sampling intervals, and FFT point counts respectively corresponding to blood flow velocities and the motion velocities of a tissue. These settings improve the image quality and accuracy of a blood flow Doppler image and tissue Doppler image. As described above, using the ultrasonic diagnostic apparatus 1 can present, for example, arteriosclerosis determination indices.

Second Embodiment

The second embodiment will be described below with reference to the accompanying drawing.

Figure 9:
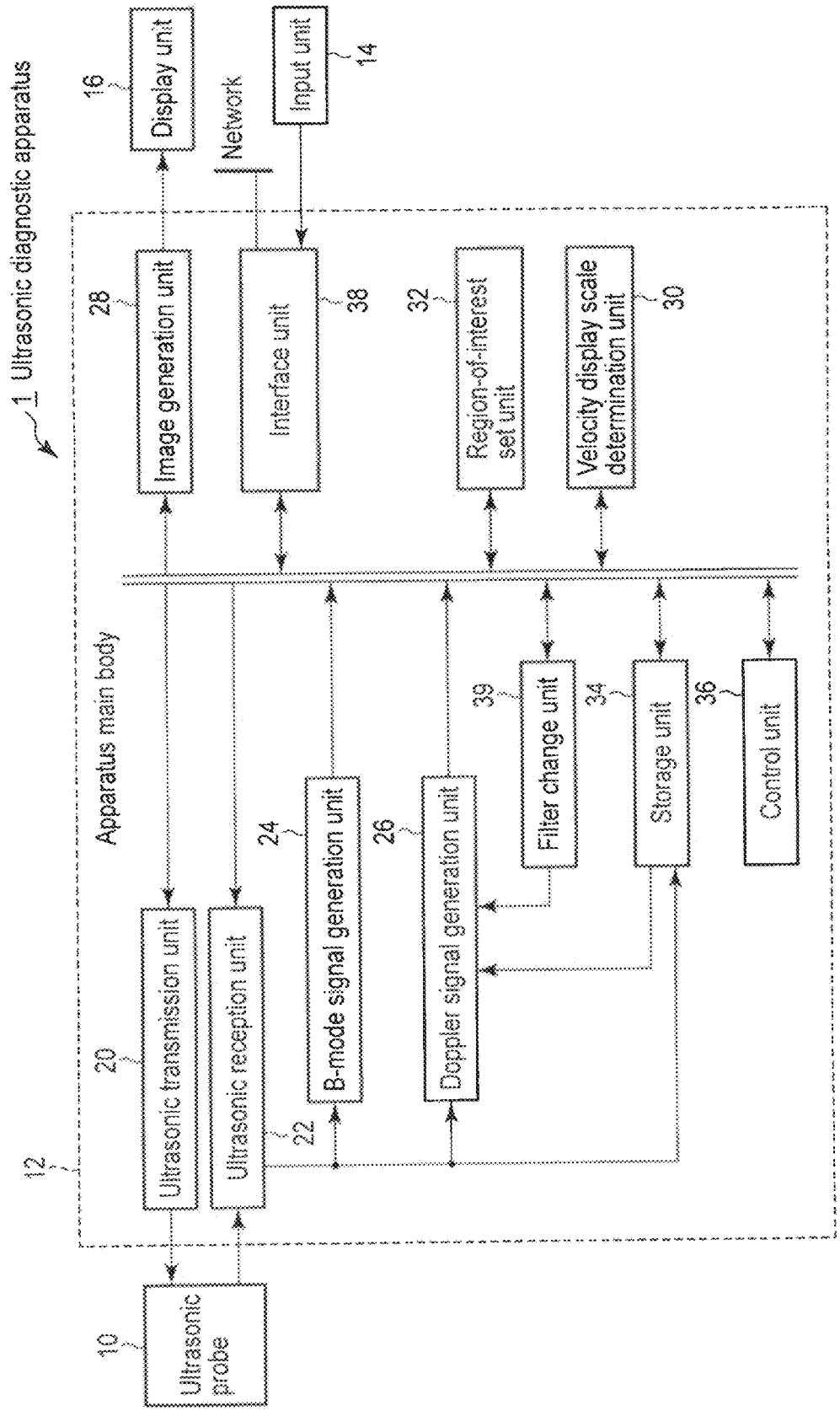
FIG. 9 is a block diagram showing the arrangement of an ultrasonic diagnostic apparatus according to the second embodiment.

FIG. 9 is a block diagram showing the arrangement of an ultrasonic diagnostic apparatus according to the second embodiment. This embodiment differs from the first embodiment in that it changes the filter characteristics of a filter included in a Doppler signal generation unit 26 in accordance with freeze operation of the operator via an input unit 14.

Figure 10:
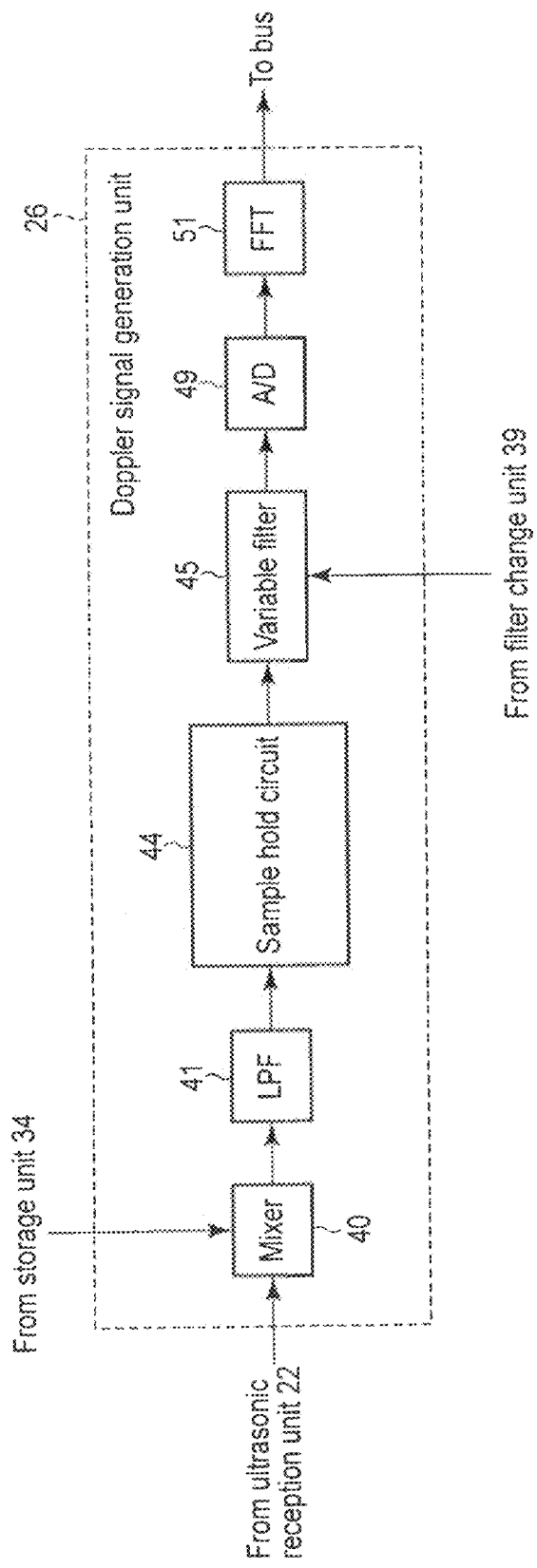
FIG. 10 is a block diagram showing the arrangement of a Doppler signal generation unit in the ultrasonic diagnostic apparatus in FIG. 9 according to the second embodiment.

An apparatus main body 12 includes a filter change unit 39 in addition to the constituent elements of the first embodiment. The Doppler signal generation unit 26 will be described first with reference to FIG. 10. FIG. 10 is a block diagram showing the arrangement of the Doppler signal generation unit 26 in an ultrasonic diagnostic apparatus 1 according to the second embodiment. The Doppler signal generation unit 26 includes a mixer 40, a low-pass filter (to be referred to as an LPF hereinafter) 41, a sample hold circuit (to be referred to as SH hereinafter) circuit 44, a variable filter 45, an analog/digital converter (to be referred to as an A/D hereinafter) 49, and a frequency analyzer (fast Fourier transform to be referred to as an FFT hereinafter) 51.

The mixer 40 multiplies the signal output from an ultrasonic reception unit 22 or a storage unit 34 by a reference signal having a frequency f0 equal to a transmission frequency. This multiplication will yield a signal having a Doppler shift frequency fd (to be referred to as a Doppler signal hereinafter) and a signal having a frequency component (2f0+fd). The LPF 41 removes a signal having a high frequency component (2f0+fd) from the signal having the two types of frequency components from the mixer.

The SH circuit 44 samples and holds part of a Doppler signal in accordance with sampling pulses from a range gate circuit (not shown). The range gate circuit generates a sampling pulse with a predetermined pulse width at a timing delayed from a rate pulse by a predetermined delay time. The predetermined delay time is the time taken for an ultrasonic wave to reciprocally propagate the distance between a piezoelectric transducer and the range gate (also called a sampling point or sampling volume) set at the depth desired by the operator. A region-of-interest set unit 32 sets a range gate in accordance with an instruction from the operator via the input unit 14. A range gate is provided in a region of interest (to be referred to as an ROI hereinafter) set on the B-mode image displayed on the display unit 16.

The SH circuit 44 outputs a sampled/held signal (to be referred to as an SH signal hereinafter) to the variable filter 45 (to be described later). In addition, a sampling interval may be determined based on the velocity display scale determined by a velocity display scale determination unit 30 (to be described later). At this time, the apparatus changes the sampling interval from the sampling interval for obtaining a blood flow Doppler signal to the sampling interval for obtaining a tissue Doppler signal in response to a freeze instruction from the operator via the input unit 14. Note that a sampling interval may be set in accordance with a blood flow velocity and the motion velocity of a tissue.

The variable filter 45 has a filter characteristic for extracting a blood flow Doppler signal from an SH signal (for example, wall filter ON or high-pass filter to be referred to as a blood flow Doppler extraction filter hereinafter) and a filter characteristic for extracting a tissue Doppler signal from the SH signal (for example, wall filter OFF or low-pass filter to be referred to as a tissue Doppler extraction filter hereinafter). The variable filter 45 changes the filter characteristics from the blood flow Doppler extraction filter to the tissue Doppler extraction filter in accordance with an output from the filter change unit 39 (to be described later). The signal filtered by the blood flow Doppler extraction filter (to be referred to as a blood flow Doppler signal hereinafter) is output to the A/D 49. The signal filtered by the tissue Doppler extraction filter (to be referred to as a tissue Doppler signal hereinafter) is output to the A/D 49. The A/D 49 converts an input signal into a digital signal.

The FFT 51 executes frequency analysis for the signal converted into the digital signal by fast Fourier transform. The FFT 51 generates a frequency spectrum based on the frequency analysis result. The FFT 51 outputs the generated frequency spectrum to the image generation unit 28 (to be described later) and the velocity display scale determination unit 30 (to be described later). More specifically, the FFT 51 generates a blood flow Doppler spectrum by executing frequency analysis for the blood flow Doppler signal converted into the digital signal. The FFT 51 generates a tissue Doppler spectrum by executing frequency analysis for the tissue Doppler signal converted into the digital signal. The FFT 51 generates a tissue Doppler spectrum by executing frequency analysis for the tissue Doppler signal converted into the digital signal.

Note that a point count (to be referred to as an FFT point count hereinafter) in fast Fourier transform by the FFT 51 may be set in accordance with a blood flow velocity and the motion velocity of a tissue. In addition, an FFT point count may be determined based on the velocity display scale determined by the velocity display scale determination unit 30.

The filter change unit 39 changes the filter characteristics of the variable filter 45 (to be described later) of the Doppler signal generation unit 26 in response to a freeze instruction from the operator via the input unit 14. More specifically, the filter change unit 39 changes the filter characteristics of the variable filter 45 from the blood flow Doppler extraction filter to the tissue Doppler extraction filter.

The storage unit 34 stores the reception signal generated by the ultrasonic reception unit 22. The storage unit 34 outputs a reception signal stored in the storage unit 34 to the Doppler signal generation unit 26 in response to a freeze instruction from the operator via the input unit 14.

In response to a freeze instruction from the operator via the input unit 14, an image generation unit 28 generates a blood flow Doppler image (to be referred to as a blood flow Doppler center image hereinafter) on which the input time of the freeze instruction (to be referred to as a freeze input time hereinafter) is located at the center of the abscissa (time axis) of the blood flow Doppler waveform. The image generation unit 28 generates a tissue Doppler image after the freeze input time based on the tissue Doppler spectrum output from the Doppler signal generation unit 26. The image generation unit 28 generates a superimposed image by superimposing the tissue Doppler image on the blood flow Doppler center image. The image generation unit 28 generates a combined image by combining the superimposed image with a B-mode image.

When the operator operates the FREEZE button, the input device 14 finishes the transmission/reception of ultrasonic waves, and the ultrasonic diagnostic apparatus 1 is set in a pause state. The input unit 14 outputs a signal concerning the operation of the FREEZE button to the filter change unit 39, the storage unit 34, and the image generation unit 28.

(Filter Characteristic Changing Function)

The filter characteristic changing function is a function of changing the filter characteristics of a filter included in the Doppler signal generation unit 26 in accordance with the freeze operation by the operator via the input unit 14. Processing based on the filter characteristic changing function (to be referred to as filter characteristic changing processing hereinafter).

FIG. 11 is a flowchart showing a procedure for filter characteristic changing processing.

The ultrasonic reception unit 22 generates a reception signal (step Sb1). The storage unit 34 stores the generated reception signal (step Sb2). The apparatus generates a blood flow Doppler waveform based on the reception signal (step Sb3). At this time, the filter characteristic used by the variable filter 45 corresponds to the blood flow Doppler extraction filter. A display unit 16 displays the blood flow Doppler waveform with the first velocity display scale (step Sb4). When the operator inputs a freeze instruction via the input unit 14 (step Sb5), the apparatus generates a blood flow Doppler center image. The display unit 16 displays the generated blood flow Doppler center image (step Sb6).

In response to the input of the freeze instruction, the filter change unit 39 changes the filter characteristics of the variable filter 45 from the blood flow Doppler extraction filter to the tissue Doppler extraction filter (step Sb7). The Doppler signal generation unit 26 generates a tissue Doppler waveform based on the reception signal stored in the storage unit 34 (step Sb8). The tissue Doppler waveform generated by the processing in step Sb8 is a tissue Doppler waveform after the input of the freeze instruction. Note that the processing in step Sb8 may generate tissue Doppler waveforms before and after freeze operation. The apparatus generates a superimposed image by superimposing the generated tissue Doppler waveform on the blood flow Doppler waveform with the second velocity display scale. The display unit 16 displays the generated superimposed image (step Sb9).

Figure 12:
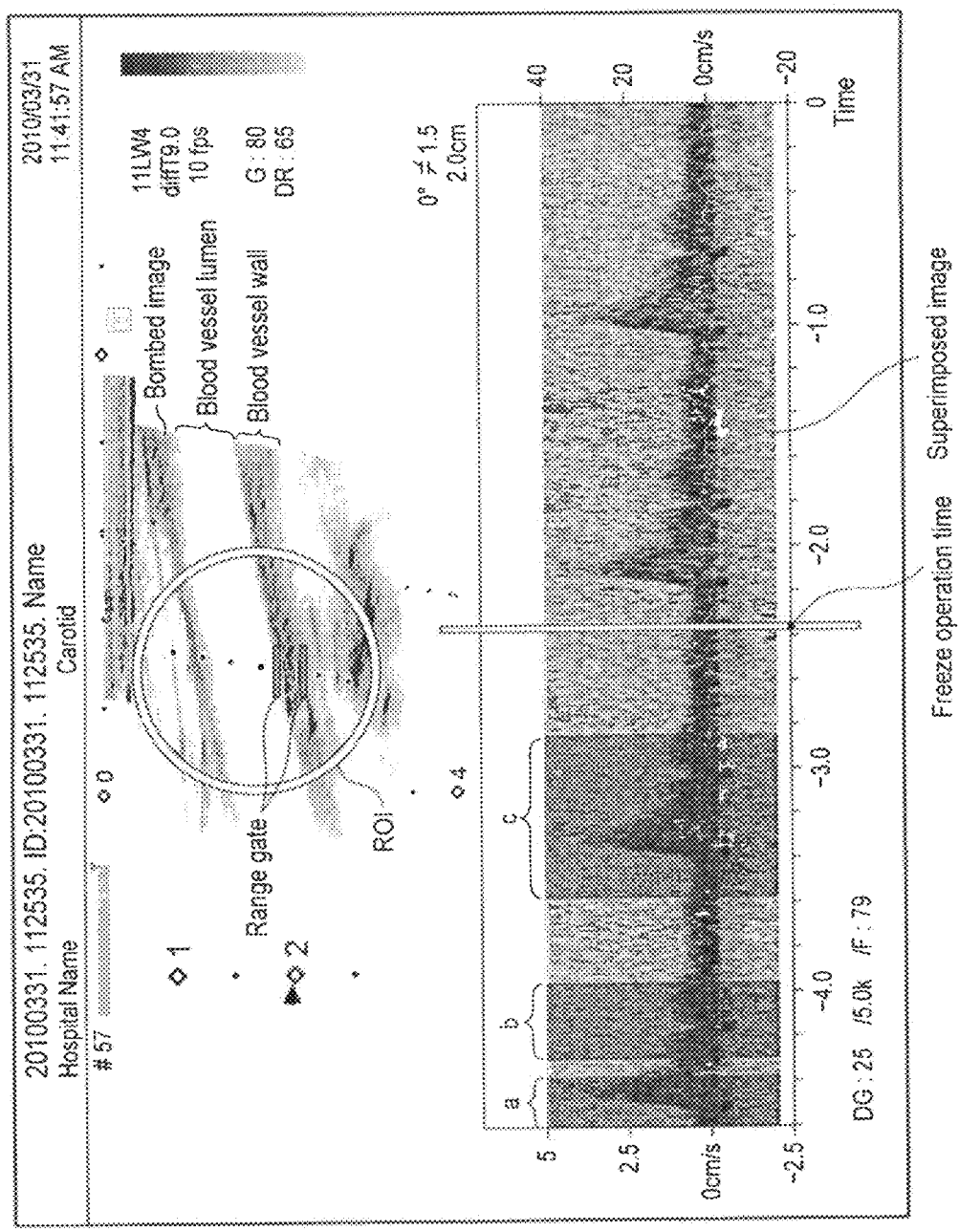
FIG. 12 is a view showing an example of a superimposed view obtained by superimposing, on a blood flow Doppler waveform, hues changed in accordance with the intensity values of a tissue Doppler signal before freeze operation and a tissue Doppler waveform after freeze operation while making them temporally match each other with the respective velocity display scales according to the second embodiment.

FIG. 12 shows an example of a superimposed view obtained by superimposing, on a blood flow Doppler waveform, hues changed in accordance with the intensity values of a frequency spectrum before freeze operation, which is generated by the SH circuit 44 without via the variable filter 45, and a tissue Doppler waveform after freeze operation. The blood flow Doppler waveform in FIG. 12 is displayed with the first velocity display scale. The tissue Doppler waveform in FIG. 12 is displayed with the second velocity display scale. When superimposing a tissue Doppler waveform on a blood flow Doppler waveform, the apparatus superimposes them while making each time of the time axis of the blood flow Doppler waveform match a corresponding time of the time axis of the tissue Doppler waveform. Note that the intensity values of the frequency spectrum before freeze operation may be the intensity values of the tissue Doppler spectrum before freeze operation.

The apparatus displays the ROI set on the B-mode image in FIG. 12 in accordance with an instruction from the operator via the input unit 14. The apparatus displays, in the ROI, the range gate set in accordance with an instruction from the operator via the input unit 14. Note that the range gate includes the blood vessel lumen and the blood vessel wall. The ordinate on the right side of the superimposed image in FIG. 12 is an axis representing the velocity concerning the blood flow Doppler waveform. The ordinate on the left side of the superimposed image in FIG. 12 is an axis representing the velocity concerning the tissue Doppler waveform. A vertical line representing a freeze operation time is displayed at the center of the abscissa on the superimposed image.

Regions a, b, and c on the superimposed image in FIG. 12 correspond to intervals in which frequency intensities on the tissue Doppler spectrum exceed a threshold intensity. The apparatus changes the hue of the background of a superimposed in the same manner as in the modification of the first embodiment.

FIG. 13 shows an example of a superimposed view obtained by superimposing, on a blood flow Doppler waveform, hues changed in accordance with the intensity values of a tissue Doppler signal after freeze operation and a tissue Doppler waveform after freeze operation. The blood flow Doppler waveform in FIG. 13 is displayed with the first velocity display scale. The tissue Doppler waveform in FIG. 13 is displayed with the second velocity display scale. When superimposing a tissue Doppler waveform on a blood flow Doppler waveform, the apparatus superimposes them while making each time of the time axis of the blood flow Doppler waveform match a corresponding time of the time axis of the tissue Doppler waveform. The apparatus displays the ROI set on the B-mode image in FIG. 13 in accordance with an instruction from the operator via the input unit 14. The apparatus displays, in the ROI, the range gate set in accordance with an instruction from the operator via the input unit 14. Note that the range gate includes the blood vessel lumen and the blood vessel wall. The ordinate on the right side of the superimposed image in FIG. 13 is an axis representing the velocity concerning the blood flow Doppler waveform. The ordinate on the left side of the superimposed image in FIG. 13 is an axis representing the velocity concerning the tissue Doppler waveform. A vertical line representing a freeze operation time is displayed at the center of the abscissa on the superimposed image.

Regions d and e on the superimposed image in FIG. 13 correspond to intervals in which the frequencies of the blood flow Doppler spectrum exceed a threshold frequency. The apparatus changes the hue of the background of a superimposed image based on a tissue Doppler spectrum in the same manner as in the modification of the first embodiment.

According to the above arrangement, the following effects can be obtained.

The ultrasonic diagnostic apparatus 1 can generate a blood flow Doppler waveform and a tissue Doppler waveform based on a reception signal in an ROI in one azimuth direction by changing the filter characteristics of the Doppler signal generation unit 26. In addition, the apparatus can display a blood flow Doppler waveform and a tissue Doppler waveform with the first and second velocity display scales. These features allow the operator to easily observe displayed images. In addition, the ultrasonic diagnostic apparatus 1 can generate a tissue Doppler waveform in response to freeze operation by the operator by storing a reception signal in the storage unit 34. The apparatus can also change the hue or luminance of the background of a tissue Doppler image in accordance with the frequency or frequency intensity of the tissue Doppler waveform. In addition, the arrangement of the Doppler signal generation unit 26 can be simplified, and hence the cost of the ultrasonic diagnostic apparatus 1 can be reduced.

Third Embodiment

The third embodiment will be described below with reference to the accompanying drawing.

Figure 14:
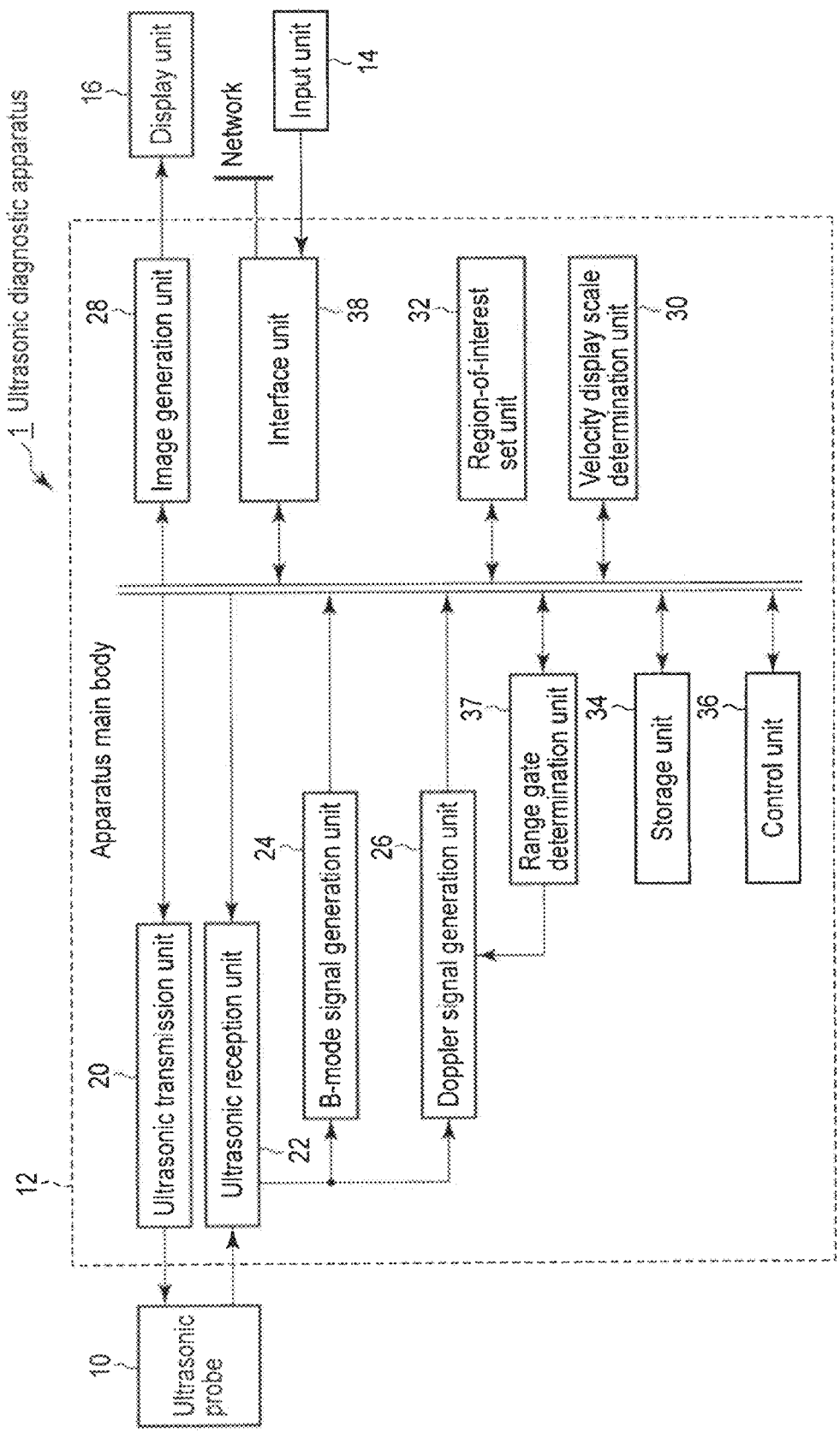
FIG. 14 is a block diagram showing the arrangement of an ultrasonic diagnostic apparatus according to the third embodiment.

FIG. 14 is a block diagram showing the arrangement of an ultrasonic diagnostic apparatus according to the third embodiment. This embodiment differs from the first and second embodiments in that it sets a plurality of range gates in an ROI based on the pixel values in the ROI, and generates a Doppler image for each set range gate. An apparatus main body 12 includes a range gate determination unit 37 in addition to the constituent elements of the first embodiment.

A region-of-interest set unit 32 sets an ROI on the B-mode image displayed on a display unit 16 in accordance with an instruction input from the operator via an input unit 14.

The range gate determination unit 37 determines the positions of a plurality of range gates in the ROI based on the pixel values in the ROI. The positions of range gates are set in one azimuth direction. For the sake of simplicity, assume that two types of range gates are determined in an ROI. One type is a range gate for blood flow Doppler (to be referred to as a blood flow RG hereinafter), and the other type is a range gate for tissue Doppler (to be referred to as a tissue RG hereinafter). The range gate determination unit 37 determines the position of the tissue RG in the ROI in accordance with an instruction from the operator via the input unit 14. Note that a blood flow RG may be determined in place of a tissue RG. The range gate determination unit 37 may determine a tissue RG by comparing the pixel values in the ROI with the typical pixel value of a tissue stored in a memory (not shown).

The range gate determination unit 37 calculates a difference value for each of a plurality of pixels along a scanning line direction from the tissue RG by subtracting the pixel values of two adjacent pixels from each other. Note that the range gate determination unit 37 may calculate the absolute value of a difference value instead of the difference value. The range gate determination unit 37 reads out a predetermined value stored in a storage unit 34. If the calculated difference value is equal to more than the predetermined threshold, the range gate determination unit 37 determines the interval between the two pixels concerning the difference value as the boundary between the tissue and the blood vessel lumen. The predetermined value is, for example, the difference between the pixel value of the blood vessel lumen and the pixel value of the blood vessel wall.

The range gate determination unit 37 calculates the distance from the determined boundary pixel to one end of the tissue RG (to be referred to as the first distance hereinafter) along the scanning line direction. The range gate determination unit 37 calculates the distance from the determined boundary pixel to the other end of the tissue RG (to be referred to as the second distance hereinafter) along the scanning line direction. The range gate determination unit 37 calculates the distance (to be referred to as the half distance hereinafter) by dividing the longer one of the first and second distances by two. The range gate determination unit 37 sets a blood flow RG at a position spaced apart from the boundary by the half distance inside the tissue RG. FIG. 15 is a view showing an example of the tissue RG and the blood flow RG determined in the ROI set on the B-mode image displayed by the display unit 16.

Note that the range gate determination unit 37 may determine the position of a tissue RG along with one blood flow wall in an ROI in accordance with an instruction from the operator via the input unit 14. At this time, the range gate determination unit 37 determines the boundary between the other blood vessel wall and the blood vessel lumen. The range gate determination unit 37 sets a blood flow RG at the middle position between the boundary between one blood vessel wall and the blood vessel lumen and the boundary between the other blood vessel wall and the blood vessel lumen. FIG. 16 is a view showing an example of a tissue RG and a blood flow RG determined in an ROI set on the B-mode image displayed by the display unit 16.

The range gate determination unit 37 generates a delay time (to be referred to as a blood flow RG time hereinafter) corresponding to the position (depth) of a blood flow RG. The blood flow RG time is the time taken for an ultrasonic wave to reciprocally propagate the distance between the blood flow RG and a piezoelectric transducer. The range gate determination unit 37 generates a delay time (to be referred to as a tissue RG time hereinafter) corresponding to the position (depth) of a tissue flow RG. The tissue RG time is the time taken for an ultrasonic wave to reciprocally propagate the distance between the tissue RG and a piezoelectric transducer. The range gate determination unit 37 generates a sampling pulse with a predetermined pulse width (to be referred to as a blood flow sampling pulse hereinafter) at a timing delayed from a rate pulse by the blood flow RG time. The range gate determination unit 37 generates a sampling pulse with a predetermined pulse width (to be referred to as a tissue sampling pulse hereinafter) at a timing delayed from a rate pulse by the tissue RG time. The range gate determination unit 37 outputs a blood flow sampling pulse to a first sample hold circuit (to be referred to as a first SH circuit hereinafter) 44. The range gate determination unit 37 outputs a tissue sampling pulse to a second sample hold circuit (to be referred to as a second SH circuit hereinafter) 51.

Figure 17:
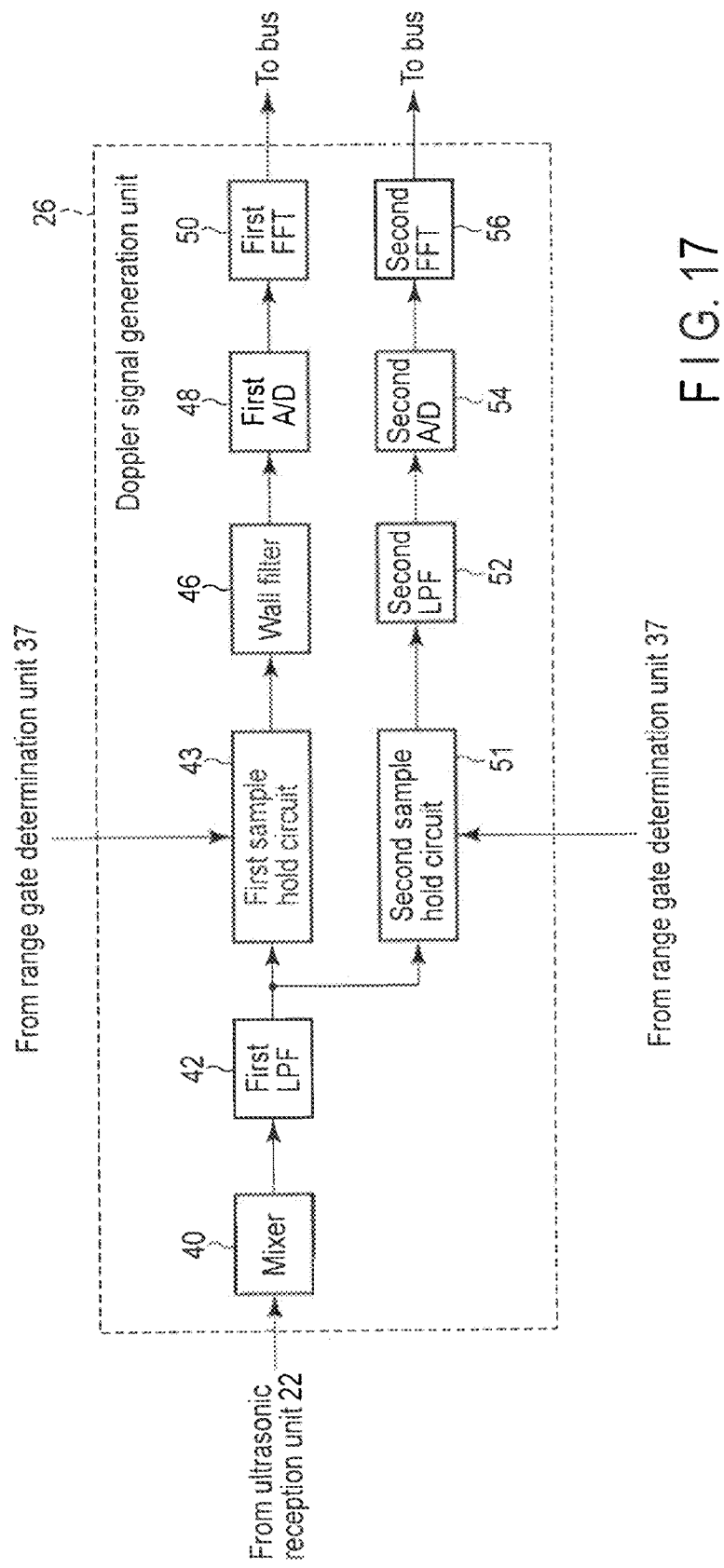
FIG. 17 is a block diagram showing the arrangement of a Doppler signal generation unit in the ultrasonic diagnostic apparatus in FIG. 14 according to the third embodiment.

The Doppler signal generation unit 26 will be described with reference to FIG. 17. FIG. 17 is a block diagram showing the arrangement of a Doppler signal generation unit 26 in the ultrasonic diagnostic apparatus 1 of this embodiment. The Doppler signal generation unit 26 includes a mixer 40, a first low-pass filter (to be referred to as a first LPF hereinafter) 42, the first sample hold (to be referred to as SH hereinafter) circuit 43, a wall filter 46, a first analog/digital converter (to be referred to as a first A/D hereinafter) 48, a first frequency analyzer (Fast Fourier Transform (to be referred to as a first FFT hereinafter) 50, a second SH circuit 51, a second low-pass filter (to be referred to as a second LPF hereinafter) 52, a second analog/digital converter (to be referred to as a second A/D hereinafter) 54, and a second frequency analyzer (Fast Fourier Transform to be referred to as a second FFT hereinafter) 56.

The mixer 40 multiplies the signal output from the ultrasonic reception unit 22 by a reference signal having a frequency f0 equal to the transmission frequency. This multiplication yields a signal having a Doppler shift frequency fd (to be referred to as a Doppler signal hereinafter) and a signal having a frequency component (2f0+fd). The first LPF 42 removes the signal of the high frequency component (2f0+fd) from the signal having the two types of frequency components from the mixer.

The first SH circuit 43 samples and holds part of a Doppler signal in accordance with a blood flow sampling pulse The wall filter 46 removes a Doppler signal (to be referred to as a blood flow Doppler signal hereinafter) corresponding to a velocity attributed to the motion of a blood vessel wall, cardiac valve, or the like from an output from the first SH circuit 43 to extract a Doppler signal (to be referred to as a blood flow Doppler signal hereinafter) attributed to a blood flow. The wall filter 46 outputs a blood flow Doppler signal to the first A/D 48. The first A/D 48 converts the blood flow Doppler signal to a digital signal.

The first FFT 50 executes frequency analysis of the blood flow Doppler signal converted into the digital signal by fast Fourier transform. The first FFT 50 generates the frequency spectrum of the blood flow Doppler signal based on the frequency analysis result. The first FFT 50 outputs the frequency spectrum of the blood flow Doppler signal (to be referred to as a blood flow Doppler spectrum hereinafter) to an image generation unit 28 (to be described later) and a velocity display scale determination unit 30 (to be described later). The blood flow Doppler spectrum indicates the frequency of the blood flow Doppler signal and the intensity of the frequency as a function of time. The frequency of the blood flow Doppler signal corresponds to the blood flow velocity.

The second SH circuit 51 samples and holds part of a Doppler signal based on a tissue sampling pulse.

The second LPF 52 removes the blood flow Doppler signal from the output from the second SH circuit 51 to extract a tissue Doppler signal. The second LPF 52 outputs the tissue Doppler signal to the second A/D 54. The second A/D 54 converts the tissue Doppler signal to a digital signal.

The second FFT 56 executes frequency analysis of the tissue Doppler signal converted into the digital signal by fast Fourier transform.

The second FFT 56 generates the frequency spectrum of the tissue Doppler signal based on the frequency analysis result. The second FFT 56 outputs the frequency spectrum of the tissue Doppler signal (to be referred to as a tissue Doppler spectrum hereinafter) to the image generation unit 28 (to be described later) and the velocity display scale determination unit 30 (to be described later). The tissue Doppler spectrum indicates the frequency of the tissue Doppler signal and the intensity of the frequency in association with the time. The frequency of the tissue Doppler signal corresponds to the motion velocity of the tissue. For the sake of simplicity, assume that the motion velocity of the tissue is the motion velocity of the blood vessel wall.

The image generation unit 28 maps B-mode signals in a dedicated memory in accordance with position information (mapping processing). The image generation unit 28 then interpolates B-mode signals between ultrasonic scanning lines (interpolation processing). The image generation unit 28 generates a B-mode image constituted by a plurality of pixels by mapping processing and interpolation processing. Each pixel has a pixel value corresponding to the intensity (amplitude) of a corresponding B-mode signal.

The image generation unit 28 generates a blood flow Doppler image based on the blood flow Doppler spectrum output from the Doppler signal generation unit 26. A blood flow Doppler image is an image indicating a waveform (to be referred to as a blood flow Doppler waveform hereinafter) representing the signal intensities of a blood flow Doppler signal as the magnitudes of luminances or pixel values, with the ordinate representing the Doppler shift frequency attributed to a blood flow and the abscissa representing the time.

The image generation unit 28 generates a tissue Doppler image based on the tissue Doppler spectrum output from the Doppler signal generation unit 26. A tissue Doppler image is an image indicating a waveform (to be referred to as a tissue Doppler waveform hereinafter) representing the signal intensities of a tissue Doppler signal as the magnitudes of luminances or pixel values, with the ordinate representing the Doppler shift frequency attributed to a tissue (e.g., a blood vessel wall) and the abscissa representing the time.

The image generation unit 28 has a frame memory or the like (not shown). The image generation unit 28 combines character information, scale marks, or the like of various kinds of parameters on a B-mode image, blood flow Doppler waveform, or tissue Doppler waveform. The image generation unit 28 outputs the combined image to the display unit 16. The image generation unit 28 generates an image (to be referred to as a superimposed image hereinafter) by superimposing a tissue Doppler waveform on a blood flow Doppler waveform while making phases match each other. Note that the image generation unit 28 may generate a combined image by combining a superimposed image with a B-mode image. A B-mode image, blood flow Doppler waveform, and tissue Doppler waveform will be referred to as ultrasonic images hereinafter.

The storage unit 34 stores a plurality of reception delay patterns with different focus depths, control programs for the ultrasonic diagnostic apparatus 1, a diagnostic protocol, various kinds of data such as transmission/reception conditions, the B-mode signals generated by the B-mode signal generation unit 24, the blood flow Doppler spectra and tissue Doppler spectra generated by the Doppler signal generation unit 26, ultrasonic images such B-mode images, blood flow Doppler waveforms, and tissue Doppler waveforms generated by the image generation unit 28, predetermined values and the like used by the range gate determination unit 37, and the like.

The display unit 16 displays the B-mode image output from the image generation unit 28. The display unit 16 displays the superimposed image generated by the image generation unit 28. The display unit 16 displays the blood flow Doppler waveform generated by the image generation unit 28. The display unit 16 displays the tissue Doppler waveform generated by the image generation unit 28. The display unit 16 displays an ROI on a B-mode image. The display unit 16 displays a blood flow RG and a tissue RG in an ROI.

The input unit 14 inputs an ROI in accordance with an instruction from the operator. The input unit 14 inputs at least one of a tissue RG and a blood flow RG in an ROI in accordance with an instruction from the operator.

(Range Gate Determination Function)

The range gate determination function is a function of determining a plurality of range gates in the ROI set on a B-mode image based on the pixel values of a B-mode image. Processing based on the range gate determination function (to be referred to as range gate determination processing hereinafter) will be described below.

Figure 18:
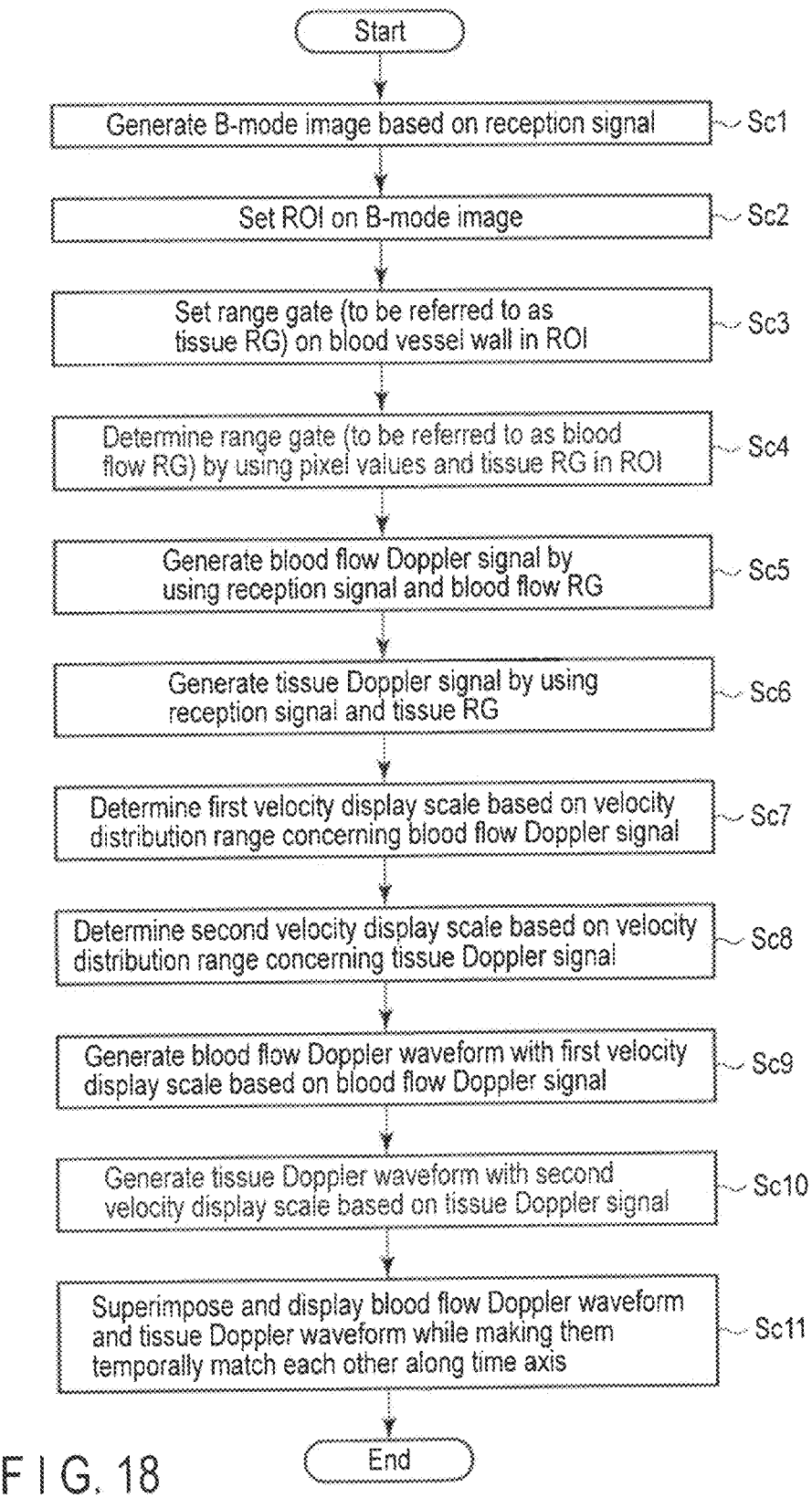
FIG. 18 is a flowchart showing a procedure for the processing of determining the positions of a plurality of range gates in a region of interest based on the pixel values in the region of interest according to the third embodiment.

FIG. 18 is a flowchart showing a procedure for range gate determination processing.

The apparatus generates a B-mode image based on a reception signal (step Sc1). The apparatus sets an ROI on the generated B-mode image (step Sc2). The apparatus sets a tissue RG in the ROI (step Sc3). The apparatus determines a blood flow RG by using the pixel values and tissue RG in the ROI (step Sc4). The apparatus determines two types of range gates respectively corresponding to a blood vessel lumen and a blood vessel wall. The apparatus generates a blood flow Doppler waveform by using the reception signal and the blood flow RG (step Sc5). The apparatus generates a tissue Doppler waveform by using the reception signal and the tissue RG (step Sc6). The apparatus determines the first velocity display scale based on a velocity distribution range concerning blood flow Doppler signals (step Sc7). The apparatus determines the second velocity display scale based on a velocity distribution range concerning tissue Doppler signals (step Sc8). The apparatus generates a blood flow Doppler waveform with the first velocity display scale based on the blood flow Doppler signal (step Sc9). The apparatus generates a tissue Doppler waveform with the second velocity display scale based on the tissue Doppler signal (step Sc10). The display unit 16 displays the superimposed image generated based on the blood flow Doppler waveform and the tissue Doppler waveform while making them temporally match each other along the time axis (step Sc11).

According to the above arrangement, the following effects can be obtained.

The ultrasonic diagnostic apparatus 1 can determine a plurality of range gates in an ROI in one azimuth direction based on the pixel values in the ROI. The apparatus can also generate a plurality of Doppler waveforms respectively corresponding to a plurality of range gates by using a reception signal in an ROI in one azimuth direction. If, for example, a plurality of range gates are two range gates determined for the blood vessel lumen and the blood vessel wall in the azimuth direction of the blood vessel lumen, the ultrasonic diagnostic apparatus 1 can generate a blood flow Doppler waveform and a tissue Doppler waveform. In addition, the apparatus can superimpose and display the blood flow Doppler waveform and the tissue Doppler waveform with the first and second velocity display scales. These features allow the operator to easily observe displayed images. In addition, according to the ultrasonic diagnostic apparatus 1, it is not necessary to perform any setting operation for a plurality of range gates. This reduces the cumbersomeness of setting a plurality of range gates, thereby improving the examination efficiency.

In the first to third embodiments, a blood flow Doppler signal and a tissue Doppler signal have been described as the first and second Doppler signals, respectively. However, the first and second Doppler signals generated in this embodiment are not limited to a blood flow Doppler signal and a tissue Doppler signal. In addition, in the first to third embodiments, the image generation unit 28 generates a blood flow Doppler image and a tissue Doppler image as the first and second Doppler images, respectively. However, the first and second Doppler images generated in this embodiment are not limited to a blood flow Doppler image and a tissue Doppler image. That is, more generally, the first Doppler signal is a Doppler signal attributed to motion in a region of interest, and the second Doppler signal is a Doppler signal attributed to motion slower than the motion in the region of interest. At this time, the first and second Doppler images generated by the image generation unit 28 are Doppler images respectively corresponding to the first and second Doppler signals. The following are specific examples of motion targets.

The first example described below concerns the first embodiment, in which a blood flow Doppler signal is used as the first Doppler signal, and a Doppler signal (to be referred to as a lymph flow Doppler signal hereinafter) attributed to the flow of lymph fluid is used as the second Doppler signal. Note that it is also possible to use a blood flow Doppler signal as the first Doppler signal and a lymph flow Doppler signal as the second Doppler signal in the second and third embodiments.

That is, a motion target concerning the first Doppler signal is blood, and a motion target concerning the second Doppler signal is a lymph fluid. In this case, the Doppler signal generation unit 26 generates the frequency spectrum of a lymph flow Doppler signal (to be referred to as a lymph flow Doppler spectrum hereinafter) based on a lymph flow Doppler signal. The velocity display scale determination unit 30 generates a velocity display scale for blood flow velocities as the first velocity display scale based on a velocity distribution range concerning a blood flow Doppler signal. The velocity display scale determination unit 30 generates a velocity display scale for lymph fluid velocities as the second velocity display scale based on a velocity distribution range concerning a lymph flow Doppler signal.

The image generation unit 28 generates a blood flow Doppler image as the first Doppler image based on the blood flow Doppler spectrum. The image generation unit 28 generates a Doppler image concerning a lymph flow (to be referred to as a lymph flow Doppler image hereinafter) as the second Doppler image based on the lymph flow Doppler spectrum. A lymph flow Doppler image is an image indicating a waveform (to be referred to as a lymph flow Doppler waveform hereinafter) representing the signal intensities of a lymph flow Doppler signal as the magnitudes of luminances or pixel values, with the ordinate representing the Doppler shift frequency attributed to a lymph flow and the abscissa representing time. The image generation unit 28 generates a superimposed image by superimposing the lymph flow Doppler waveform on a blood flow Doppler waveform while making them temporally match each other along the time axis. The display unit 16 displays the blood flow Doppler waveform in the superimposed image with the first velocity display scale, and displays the lymph flow Doppler waveform in the superimposed image with the second velocity display scale.

The ultrasonic diagnostic apparatus 1 to which the first example is applied can superimpose and display a blood flow Doppler waveform and a lymph flow Doppler waveform, at a region where a blood vessel is located close to a lymph duct, with the first and second velocity display scales respectively corresponding to a blood flow velocity and a lymph fluid velocity. This can present, for example, the state of blood circulation and the state of a lymph flow.

The second example described below concerns the first embodiment, in which a Doppler signal attributed to a blood flow in an artery (to be referred to as an arterial blood Doppler signal hereinafter) is used as the first Doppler signal, and a Doppler signal attributed to a blood flow in a vein (to be referred to as a venous blood Doppler signal hereinafter) is used as the second Doppler signal. Note that it is also possible to use an arterial blood Doppler signal as the first Doppler signal and a venous blood Doppler signal as the second Doppler signal in the second and third embodiments.

That is, a motion target concerning the first Doppler signal is blood in an artery, and a motion target concerning the second Doppler signal is a blood in a vein. In this case, the Doppler signal generation unit 26 generates the frequency spectrum of an arterial blood Doppler signal (to be referred to as an arterial blood Doppler spectrum hereinafter) based on an arterial blood Doppler signal. In addition, the Doppler signal generation unit 26 generates the frequency spectrum of a vein blood Doppler signal (to be referred to as a vein blood Doppler spectrum hereinafter) based on a vein blood Doppler signal. The velocity display scale determination unit 30 generates a velocity display scale for arterial blood velocities as the first velocity display scale based on a velocity distribution range concerning an arterial blood Doppler signal. The velocity display scale determination unit 30 generates a velocity display scale for venous blood velocities as the second velocity display scale based on a velocity distribution range concerning a venous blood Doppler signal.

The image generation unit 28 generates a Doppler image concerning an arterial blood (to be referred to as an arterial blood Doppler image hereinafter) as the first Doppler image based on an arterial blood Doppler spectrum. The image generation unit 28 generates a Doppler image concerning a venous blood (to be referred to as a venous blood Doppler image hereinafter) as the second Doppler image based on a venous blood Doppler spectrum. An arterial blood Doppler image is an image indicating a waveform (to be referred to as an arterial blood Doppler waveform hereinafter) representing the signal intensities of an arterial blood Doppler signal as the magnitudes of luminances or pixel values, with the ordinate representing the Doppler shift frequency attributed to an arterial blood flow and the abscissa representing the time. A venous blood Doppler image is an image indicating a waveform (to be referred to as a venous blood Doppler waveform hereinafter) representing the signal intensities of a venous blood Doppler signal as the magnitudes of luminances or pixel values, with the ordinate representing the Doppler shift frequency attributed to a venous blood flow and the abscissa representing the time. The image generation unit 28 generates a superimposed image by superimposing the venous blood Doppler waveform on an arterial blood Doppler waveform while making them temporally match each other along the time axis. The display unit 16 displays the arterial blood Doppler waveform in the superimposed image with the first velocity display scale, and displays the venous blood Doppler waveform in the superimposed image with the second velocity display scale.

The ultrasonic diagnostic apparatus 1 to which the second example is applied can superimpose and display an arterial blood Doppler waveform and a venous blood Doppler waveform, at a region (for example, the neck) where an artery is located close to a vein, with the first and second velocity display scales respectively corresponding to an arterial blood flow velocity and a venous blood flow velocity. This can present the states of blood circulation in both the artery and the vein. This makes it possible to present the response or the like of a venous blood flow relative to an arterial blood flow or pulsation.

Some embodiments of the present invention have been described above. However, these embodiments are presented merely as examples and are not intended to restrict the scope of the invention. These novel embodiments can be carried out in various other forms, and various omissions, replacements, and alterations can be made without departing from the gist of the invention. The embodiments and their modifications are also incorporated in the scope and the gist of the invention as well as in the invention described in the claims and their equivalents.

What is claimed is:

1. An ultrasonic diagnostic apparatus comprising:
   an ultrasonic probe;
   ultrasonic transmission circuitry, which transmits an ultrasonic wave to an object via the ultrasonic probe;
   ultrasonic reception circuitry, which generates a reception signal based on a reflected wave of the ultrasonic wave;
   Doppler signal generation circuitry, which generates a first Doppler signal and a second Doppler signal based on the reception signal, wherein the first Doppler signal is attributed to a first motion of a blood flow in a first range gate in a region of interest in a predetermined azimuthal direction, the second Doppler signal is attributed to a second motion of a tissue in a second range gate in the region of interest;
   velocity display scale determination circuitry, which determines a first velocity display scale based on a velocity distribution range for the first Doppler signal and determines a second velocity display scale based on a velocity distribution range for the second Doppler signal;
   image generation circuitry, which generates a blood flow Doppler image based on the first Doppler signal and generates a tissue Doppler image based on the second Doppler signal; and
   a monitor, which displays the blood flow Doppler image with the first velocity display scale and displays the tissue Doppler image with the second velocity display scale, wherein
   the image generation circuitry generates the tissue Doppler image with a luminance of a background of a Doppler waveform changed to a predetermined luminance, based on a frequency spectrum of the second Doppler signal, the luminance of the background distinguishing a time period during which the frequency spectrum of the second Doppler signal satisfies a predefined frequency criterion from a time during which the frequency spectrum of the second Doppler signal does not satisfy the predefined frequency criterion.

2. The apparatus of claim 1, wherein the velocity display scale determination circuitry determines, as the second velocity display scale, a velocity display scale larger than the first velocity display scale.

3. The apparatus of claim 1, wherein the velocity display scale determination circuitry determines, as the first velocity display scale, a velocity display scale smaller than the second velocity display scale.

4. The apparatus of claim 1, further comprising:
   input circuitry, which inputs a scale for determining the second velocity display scale; and
   a memory, which stores a scale for determining the second velocity display scale, wherein
   the velocity display scale determination circuitry determines the second velocity display scale based on at least one of the input scale, the stored scale, and the velocity distribution range for the second Doppler signal.

5. The apparatus of claim 1, wherein
   the Doppler signal generation circuitry further comprises a variable filter, and
   the apparatus further comprises filter change circuitry, which changes a filter characteristic of the variable filter between a characteristic for extracting the first Doppler signal from the reception signal and a characteristic for extracting the second Doppler signal from the reception signal.

6. The apparatus of claim 1, wherein the Doppler signal generation circuitry generates the second Doppler signal by performing a Fourier transformation of the reception signal using a sample count larger than a sample count used in a Fourier transformation for generation of the first Doppler signal.

7. The apparatus of claim 1, wherein the image generation circuitry generates an image in which the tissue Doppler image is superimposed on the blood flow Doppler image such that times on a time axis of the blood flow Doppler image match with times on a time axis of the tissue Doppler image.

8. The apparatus of claim 1, wherein the image generation circuitry generates the tissue Doppler image with a hue of a background of a Doppler waveform set to a predetermined hue based on a frequency spectrum of the second Doppler signal.

9. The apparatus of claim 1, wherein the ultrasonic transmission circuitry transmits the ultrasonic wave under predetermined transmission conditions corresponding to a velocity of the first motion and a velocity of the second motion, respectively.

10. The apparatus of claim 9, wherein the predetermined transmission conditions include a pulse repetition frequency.

11. The apparatus of claim 1, wherein the ultrasonic reception circuitry receives the ultrasonic wave under predetermined reception conditions corresponding to a velocity of the first motion and a velocity of the second motion, respectively.

* * * * *